US010028795B2

(12) United States Patent
Choi et al.

(10) Patent No.: US 10,028,795 B2
(45) Date of Patent: Jul. 24, 2018

(54) SURGICAL IMPLEMENT AND MANIPULATION SYSTEM INCLUDING THE SAME

(71) Applicant: SAMSUNG ELECTRONICS CO., LTD., Suwon-si (KR)

(72) Inventors: Hyun-do Choi, Yongin-si (KR); Hyung-joo Kim, Seongnam-si (KR); Ho-seong Kwak, Seoul (KR); Jong-hwa Won, Seoul (KR); Joon-kee Cho, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 916 days.

(21) Appl. No.: 13/765,167

(22) Filed: Feb. 12, 2013

(65) Prior Publication Data

US 2013/0317520 A1 Nov. 28, 2013

(30) Foreign Application Priority Data

May 25, 2012 (KR) ........................ 10-2012-0056236

(51) Int. Cl.
*A61B 34/30* (2016.01)
*A61B 34/00* (2016.01)
(Continued)

(52) U.S. Cl.
CPC .............. *A61B 34/71* (2016.02); *A61B 34/30* (2016.02); *A61B 90/11* (2016.02); *A61B 2017/2927* (2013.01); *A61B 2034/305* (2016.02)

(58) Field of Classification Search
CPC ... A61B 17/20; A61B 17/201; A61B 17/2203; A61B 2017/2905; A61B 2017/2908;
(Continued)

(56) References Cited

U.S. PATENT DOCUMENTS 3,316,912 A * 5/1967 Whitaker ......... A61B 17/22031
606/1
4,880,015 A * 11/1989 Nierman ................ A61B 10/06
30/199
(Continued)

FOREIGN PATENT DOCUMENTS

JP 2006-314703 A 11/2006
JP 2011-172787 A 9/2011
(Continued)

*Primary Examiner* — Ryan J Severson
*Assistant Examiner* — Christian Knauss
(74) *Attorney, Agent, or Firm* — Harness, Dickey & Pierce, P.L.C.

(57) ABSTRACT

A surgical implement and a manipulation system including the surgical implement may include at least one instrument including at least one joint portion. The joint portion may include a first part, a second part connected to the first part, and a force applying element for applying a force for bending (or rotating) the second part. A distance between a joint point and a force application point where a force is applied may be greater than a diameter of at least one of the first part and the second part. The instrument may further include a second joint portion spaced apart from the joint portion, and a surgical tool connected to an end portion of the second joint portion. The manipulation system may include a supporting structure, at least one instrument supported by the supporting structure, and an operating device for operating the instrument.

27 Claims, 24 Drawing Sheets

(51) Int. Cl.
*A61B 17/29* (2006.01)
*A61B 90/11* (2016.01)

(58) Field of Classification Search
CPC .... A61B 2017/2927; A61B 2017/2929; A61B 2017/2939; A61B 2019/2234; A61B 2019/2238; A61B 2019/2242; A61B 2017/2919; A61B 34/71; A61B 2034/305
See application file for complete search history.

(56) References Cited

U.S. PATENT DOCUMENTS

| | | | | |
|---|---|---|---|---|
| 5,318,008 A | * | 6/1994 | Bullard | A61B 1/0056 600/139 |
| 5,456,684 A | * | 10/1995 | Schmidt | A61B 17/29 604/35 |
| 5,817,084 A | * | 10/1998 | Jensen | B25J 9/1065 606/1 |
| 6,592,572 B1 | * | 7/2003 | Suzuta | A61B 17/062 294/115 |
| 7,930,065 B2 | | 4/2011 | Larkin et al. | |
| 8,029,516 B2 | | 10/2011 | Mohr et al. | |
| 2005/0049580 A1 | * | 3/2005 | Brock | A61B 90/50 606/1 |
| 2006/0270902 A1 | | 11/2006 | Igarashi et al. | |
| 2007/0156019 A1 | | 7/2007 | Larkin et al. | |
| 2007/0250078 A1 | * | 10/2007 | Stuart | A61B 34/37 606/130 |
| 2007/0283970 A1 | | 12/2007 | Mohr et al. | |
| 2008/0039892 A1 | * | 2/2008 | Mitsuishi | A61B 19/22 606/208 |
| 2008/0064927 A1 | | 3/2008 | Larkin et al. | |
| 2008/0065101 A1 | | 3/2008 | Larkin | |
| 2008/0300579 A1 | * | 12/2008 | Broehl | A61B 17/07207 606/1 |
| 2009/0247821 A1 | | 10/2009 | Rogers | |
| 2011/0264078 A1 | * | 10/2011 | Lipow | A61B 19/201 606/1 |
| 2013/0074637 A1 | | 3/2013 | Choi et al. | |
| 2013/0197535 A1 | | 8/2013 | Okada | |

FOREIGN PATENT DOCUMENTS

| | | |
|---|---|---|
| KR | 10-2011-0030038 A | 3/2011 |
| KR | 10-2011-0109475 A | 10/2011 |

\* cited by examiner

SURGICAL IMPLEMENT AND MANIPULATION SYSTEM INCLUDING THE SAME

CROSS-REFERENCE TO RELATED APPLICATIONS

This application claims the benefit of Korean Patent Application No. 10-2012-0056236, filed on May 25, 2012, in the Korean Intellectual Property Office, the disclosure of which is incorporated herein in its entirety by reference.

BACKGROUND

1. Field

The disclosure herein relates to a surgical implement and a manipulation system including the same.

2. Description of the Related Art

Recently, minimally invasive surgery using a surgical robot has been increasingly used, and research and development on the minimally invasive surgery have been actively performed. A surgical robot has a passive arm that may be manually operated in a preparing step before surgery and an active arm driven by an operator during surgery. The active arm includes a surgical instrument that is inserted in an object (for example, an abdominal cavity, joint portions, or the like) to perform actual surgical operations.

In order to perform surgical operations actively and effectively, a surgical instrument for applying a high operating force, having a large workspace, and capable of a dexterous motion having a high degree of freedom is required. However, it is not easy to realize a surgical robot system that satisfies the above requirements. In particular, with respect to a single port surgical robot system performing surgery through a single incision portion (opening), it is difficult to satisfy the above requirements.

SUMMARY

Provided are surgical implements capable of effectively performing surgical operations.

Provided are surgical implements capable of applying a high operating force, having a large workspace, and a dexterous motion having a high degree of freedom.

Provided are surgical implements including a joint portion that is advantageous for providing a high operating force.

Provided are surgical implements including a joint portion that is easily bent with a small force.

Provided are supporter devices (or actuators) for supporting a surgical instrument and controlling a motion of the instrument.

Provided are supporter devices (or actuators) capable of providing a surgical instrument with a remote center of motion (RCM).

Provided are supporter devices (or actuators) capable of providing a plurality of surgical instruments with RCMs different from each other.

Provided are surgical manipulation systems (surgical robot systems) including the surgical implements.

Provided are surgical manipulation systems (surgical robot systems) including the supporter devices (or actuators).

Provided are surgical manipulation systems (surgical robot systems) including the surgical instruments and the supporter devices (or actuators).

Additional aspects will be set forth in part in the description which follows and, in part, will be apparent from the description, or may be learned by practice of the presented embodiments.

According to an aspect of the present invention, a surgical manipulation system includes: a supporting structure; at least one instrument supported by the supporting structure; and an operating device for operating the instrument, wherein the instrument includes a first joint portion configured to perform a motion with at least one degree of freedom, the first joint portion comprising a first part, a second part connected to the first part to be bent with respect to the first part, and a force applying element connected to the second part to apply a force for bending the second part, and a distance between a joint point of the first part joined together with the second part and a force application point where a force is applied to the second part from the force applying element is greater than a diameter of at least one of the first part and the second part.

The force application point may be located toward the first part (closer to the head portion of the instrument) relative to the joint point, the force application point may be located on an outer side of the second part based on a direction in which the second part is bent, and the joint point may be located on an inner side of the second part based on the direction in which the second part is bent.

The force application point may be located away from the first part (further away from the head portion of the instrument) relative to the joint point, the force application point may be located on an inner side of the second part based on a direction in which the second part may be bent, and the joint point may be located on an outer side of the second part based on the direction in which the second part is bent.

A protrusion protruding toward the first part may be formed on an end portion of the second part, and the force applying element may be connected to an end portion of the protrusion.

The first part may include a groove for receiving the protrusion of the second part.

The distance between the joint point and the force application point may be about 1.5 to about 3 times longer than the diameter of the first part or the second part.

The force applying element may be an elastic body.

The force applying element may have a curved structure.

The force applying element may have a structure in which a plurality of linkage elements are connected to each other.

The instrument may further include a rotary motion portion adjacent to the first joint portion.

The instrument may further include: a second joint portion being apart from the first joint portion; and a surgical tool connected to an end portion of the second joint portion.

The second joint portion may be configured to move with at least two degrees of freedom.

The instrument may further include a rotary motion portion disposed between the first joint portion and the second joint portion, and a lower portion of the instrument including the second joint portion performs a rolling motion via the rotary motion portion.

The surgical manipulation system may further include a driving unit for controlling motions of the instrument, the driving unit being disposed on a head of the instrument.

The supporting structure may include a remote center of motion (RCM) structure for providing a RCM of the at least one instrument.

The RCM structure may include a cone-type structure having a hole in a center portion thereof, and the at least one instrument is inserted in the hole.

The at least one instrument may include a first instrument and a second instrument, and a RCM of the first instrument and a RCM of the second instrument are separated from each other.

The RCM structure may be configured to drive the at least one instrument with three degrees of freedom.

The surgical manipulation system may further include: an imaging device for photographing a region where the at least one instrument operates; and a display device for displaying images obtained by the imaging device.

According to another aspect of the present invention, a surgical manipulation system includes: a supporting structure; at least one instrument supported by the supporting structure; and an operating device for operating the instrument, wherein the supporting structure may include a remote center of motion (RCM) structure for providing a RCM of the instrument, and the instrument may include a first joint portion configured to perform at least a pitch motion, a second joint portion being apart from the first joint portion, and a surgical tool mounted on an end portion of the second joint portion.

The first joint portion may be located between the RCM point of the instrument and the second joint portion.

The first joint portion may be surrounded by a protective member.

The instrument may further include a rotary motion portion between the first joint portion and the second joint portion, and a lower portion of the instrument including the second joint portion rolls due to the rotary motion portion.

The first joint portion may include a first part, a second part connected to the first part to be bent with respect to the first part, and a force applying element connected to the second part to apply a force for bending the second part, and a distance between a joint point of the first part with the second part and a force application point where a force may be applied to the second part from the force applying element may be greater than a diameter of at least one of the first part and the second part.

The second joint portion may be configured to move with at least two degrees of freedom.

The RCM structure may have a cone-type structure or a partial cone-type structure including a region in which the at least one instrument is inserted.

The at least one instrument may include a first instrument and a second instrument, and a RCM of the first instrument and a RCM of the second instrument may be spaced apart from each other.

The RCM structure may be configured to drive the at least one instrument with three degrees of freedom.

According to another aspect of the present invention, a surgical instrument includes at least one joint portion, wherein the joint portion may include a first part, a second part connected to the first part to be bent with respect to the first part, and a force applying element connected to the second part to apply a force for bending the second part, and a distance between a joint point of the first part joined together with the second part and a force application point where a force is applied to the second part from the force applying element may be greater than a diameter of at least one of the first part and the second part.

The force application point may be located toward the first part relative to the joint point, the force application point may be located on an outer side of the second part based on a direction in which the second part is bent, and the joint point may be located on an inner side of the second part based on the direction in which the second part is bent.

The force application point may be located away from the first part relative to the joint point, the force application point may be located on an inner side of the second part based on a direction in which the second part is bent, and the joint point may be located on an outer side of the second part based on the direction in which the second part is bent.

A protrusion protruding toward the first part may be formed on an end portion of the second part, and the force applying element may be connected to an end portion of the protrusion.

The first part may include a groove for receiving the protrusion of the second part.

The distance between the joint point and the force application point may be about 1.5 to about 3 times longer than the diameter of the first part or the second part.

The force applying element may be an elastic body.

The force applying element may have a curved structure.

The force applying element may have a structure in which a plurality of linkage elements are connected to each other.

The instrument may further include a rotary motion portion adjacent to the first joint portion.

The surgical instrument may further include: a second joint portion being apart from the joint portion; and a surgical tool connected to an end portion of the second joint portion.

A rotary motion portion may be further disposed between the joint portion and the second joint portion, and a lower portion of the surgical instrument including the second joint portion may roll due to the rotary motion portion.

According to another aspect of the present invention, a surgery station includes a positioning unit; at least one supporting structure mounted to an arm of the positioning unit; and at least one instrument supported by the at least one supporting structure. The instrument may include a first joint portion to move with at least one degree of freedom, a second joint portion to move with at least two degrees of freedom, a rotary motion portion disposed between the first joint portion and second joint portion to cause rotation of the second joint portion, and a surgical tool connected to an end portion of the second joint portion to move with at least one degree of freedom. The instrument may further include a head portion disposed at a first end of the instrument, opposite a second end of the instrument to which the surgical tool is connected, and the head portion may include a plurality of motors to drive movement of the first joint portion, the second joint portion, the rotary motion portion, and the surgical tool.

The supporting structure may include an insertion hole through which the instrument is inserted and a pivot member having a mounting portion to which the head portion is coupled. The supporting structure may provide the instrument with a motion based on a remote center of motion corresponding to a crossed point formed by an intersection of a central axis passing through a center of the insertion hole, a pivot axis of the pivot member, and an extension axis of the instrument, wherein the crossed point may be located between the head portion and the first joint portion.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
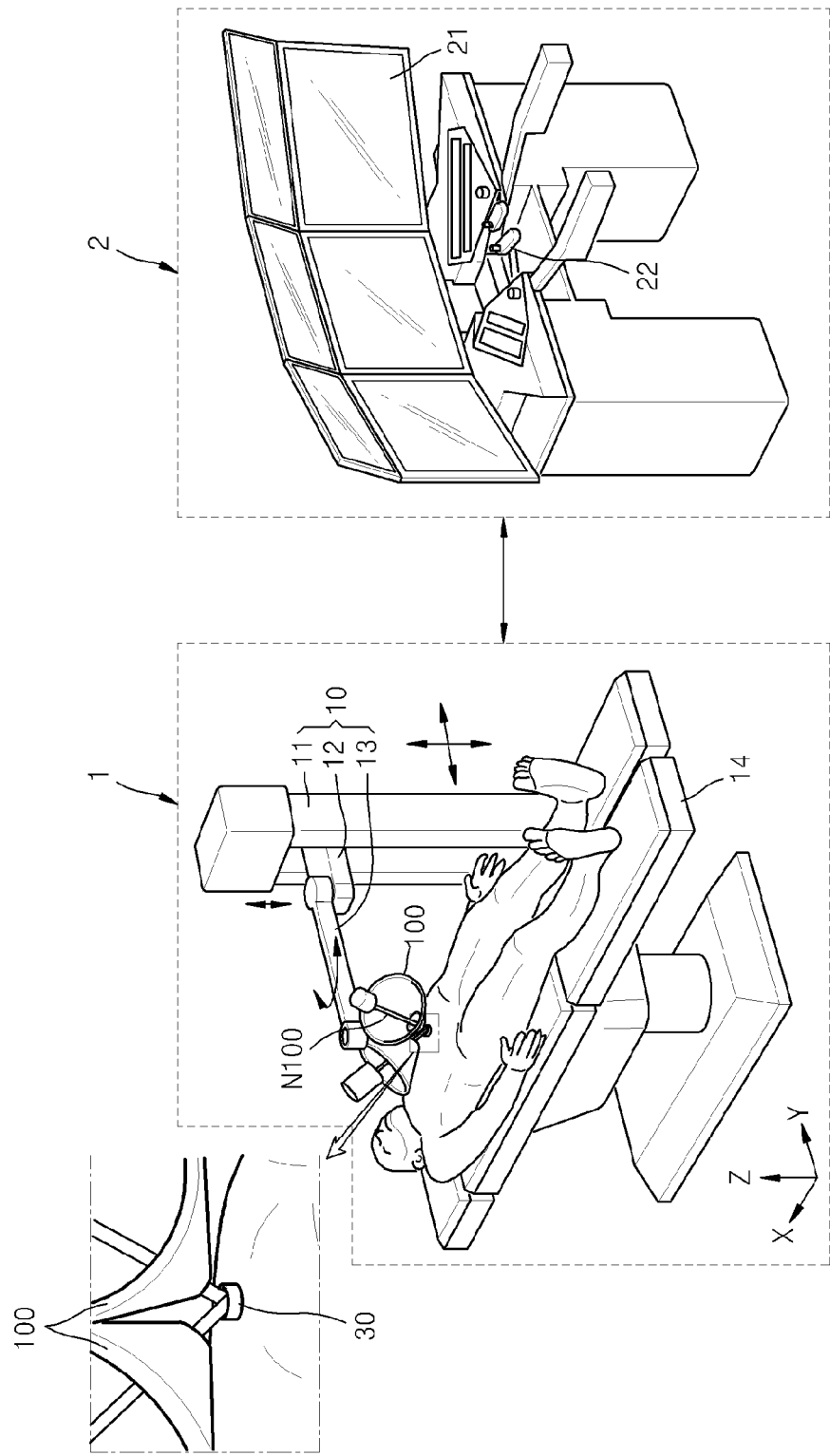
FIG. 1 is a schematic diagram of a surgical robot system (surgical manipulation system) according to an embodiment of the present invention.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

FIG. 1 is a schematic perspective view of a surgical robot system. The surgical robot system of FIG. 1 may be a surgical manipulation system.

Referring to FIG. 1, the surgical robot system (surgical manipulation system) is a system for inserting one or more instruments N100 into an object through an incision port 30, and performing a surgical operation by remotely controlling the instrument N100 while observing an inside of the object via camera images (obtained via an endoscope, for example). The surgical robot system includes a surgery station on which mechanical devices for performing surgical operations on the object are mounted, and a control station 2 for controlling the surgery station 1.

The surgery station 1 includes a supporter device 100 for supporting the instrument N100, and a positioning unit 10 for moving the supporter device 100 to a desired location, for example, a location facing the incision port 30 of the object. Here, it is noted that the surgery station 1 including the positioning unit 10 for moving the supporter device 100 may be positioned in a surgery site as needed to perform a desired operation. The surgery station 1 including the positioning unit 10 for moving the supporter device 100 may be integrated or separately disposed (e.g., the supporter device 100 may be detachable from the positioning unit 10, and the instrument N100 may be detachable from the supporter device 100). Further, the surgery station 1 may be portable, may be fixed, or may be detachably disposed to a site (e.g., the railing of an operating table, or other object).

For example, the positioning unit 10 may include a vertical column 11 including an elevation block 12 for elevating in an up-and-down direction, that is, a Z-axis direction, and a positioning arm 13 having an end portion on which the supporter device 100 is mounted. The vertical column 11 may be moved in a transverse direction, for example, an X-axis direction and/or a Y-axis direction. For example, the vertical column 11 may be moved in the X-axis direction and/or the Y-axis direction with respect to an operation table 14 on which the object is laid. Moreover, the positioning arm 13 may be coupled to the elevation block 12 to be rotatable with respect to, for example, the Z-axis direction. In FIG. 1, two supporter devices 100 are mounted on the end portion of the positioning arm 13; however, the present invention is not limited thereto. If necessary, one, three, or more supporter devices 100 may be mounted on the end portion of the positioning arm 13.

The control station 2 may include an image display unit 21 for displaying images transferred from an imaging device inserted in the object, for example, an endoscope camera, and a manipulation unit 22. The image display unit 21 may include a liquid crystal display (LCD) or light emitting diode (LED) display, for example. However, the disclosure is not so limited and may include other types of displays. The manipulation unit 22 refers to a unit for controlling the positioning unit 10, the supporter device 100, and the instrument N100 and may include, for example, one or more haptic manipulating devices such as a joystick. The manipulation unit 22 may also include a plurality of buttons, keys, keyboard, pedal or footswitch, or a mouse to enable an operator to control the surgical robot including the positioning unit 10, supporter device, 100, and instrument N100. The manipulation unit 22 may further have additional features to assist the user in operating the surgical robot, including haptic feedback capability, head-mounted displays, or virtual reality devices, for example. A driving unit for driving the supporter device 100, which will be described later, and a head portion (H10, refer to FIG. 2) of the instrument N100 are connected to the control station 2. An operator may drive the instrument N100 to perform surgical operations by operating the supporter device 100 and the instrument N100. Therefore, the control station 2 may be an operating device for controlling operations of mechanical devices of the surgery station 1. Communication may be performed among the control station 2, the positioning unit 10, the supporter device 100, and the instrument N100, over a wired or wireless network, or a combination thereof. There may be a plurality of control stations 2 which may be used by two or more operators to perform an operation (e.g., a surgery) simultaneously using two or more instruments N100. For example, a first operator may control a first instrument supported by a first supporter device, and a second operator may control a second instrument supported by a second supporter device. Alternatively, the first operator may control the first instrument supported by a first supporter device, and the second operator may control a second instrument which is also supported by the first supporter device. Other variations are further possible.

Figure 2:
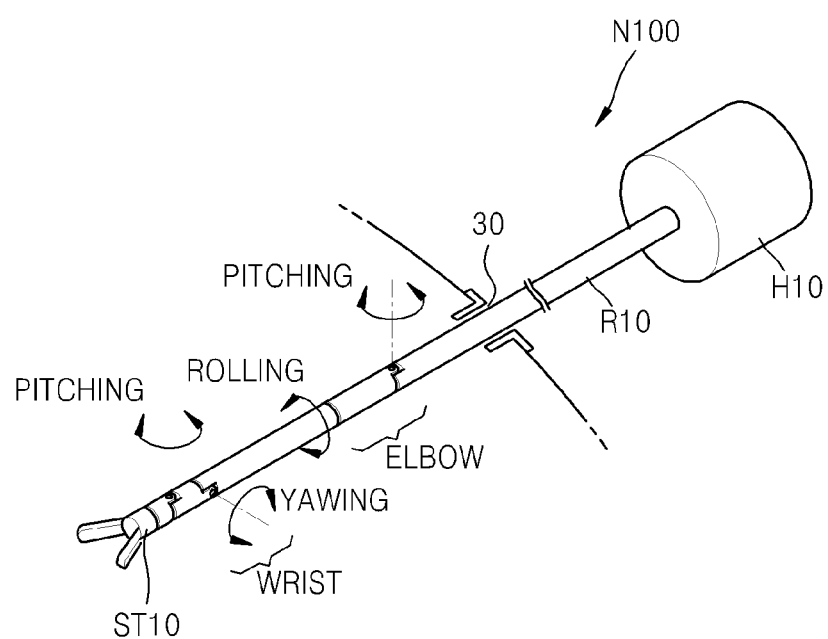
FIG. 2 is a perspective view of a surgical instrument according to an embodiment of the present invention.

FIG. 2 shows an example of the instrument N100. Referring to FIG. 2, the instrument N100 may include an extension portion R10 and the head portion H10. The extension portion R10 may be a long rod type that may be inserted into an abdominal cavity or joints of the object in order to approach a diseased part. A surgical tool ST10 for performing detailed surgical operations such as cutting or suturing according to a manipulation of the operator is mounted on an end portion of the extension portion R10. The surgical tool ST10 may be, for example, a needle holder, micro-dissector, staple applier, tacker, suction irrigation tool, clip applier, cutting blade, irrigator, catheter, suction orifice, surgical knife, surgical forceps, scissors, a cautery (a tool for burning or cutting a diseased part by using electric energy or heat energy), endoscope camera, or the like. The extension portion R10 includes at least one joint portion having a degree of freedom sufficient for performing various surgical operations. For example, the joint portion may include a wrist portion adjacent to the surgical tool ST10, and an elbow portion separated from the wrist portion. The wrist portion may be a joint capable of pitching and/or yawing. The elbow portion may be a joint capable of pitching and/or rolling. The head portion H10 includes a driving unit for driving the joint portion and the surgical tool ST10. The structure of the instrument N100 will be described later with reference to FIG. 19.

Figure 3:
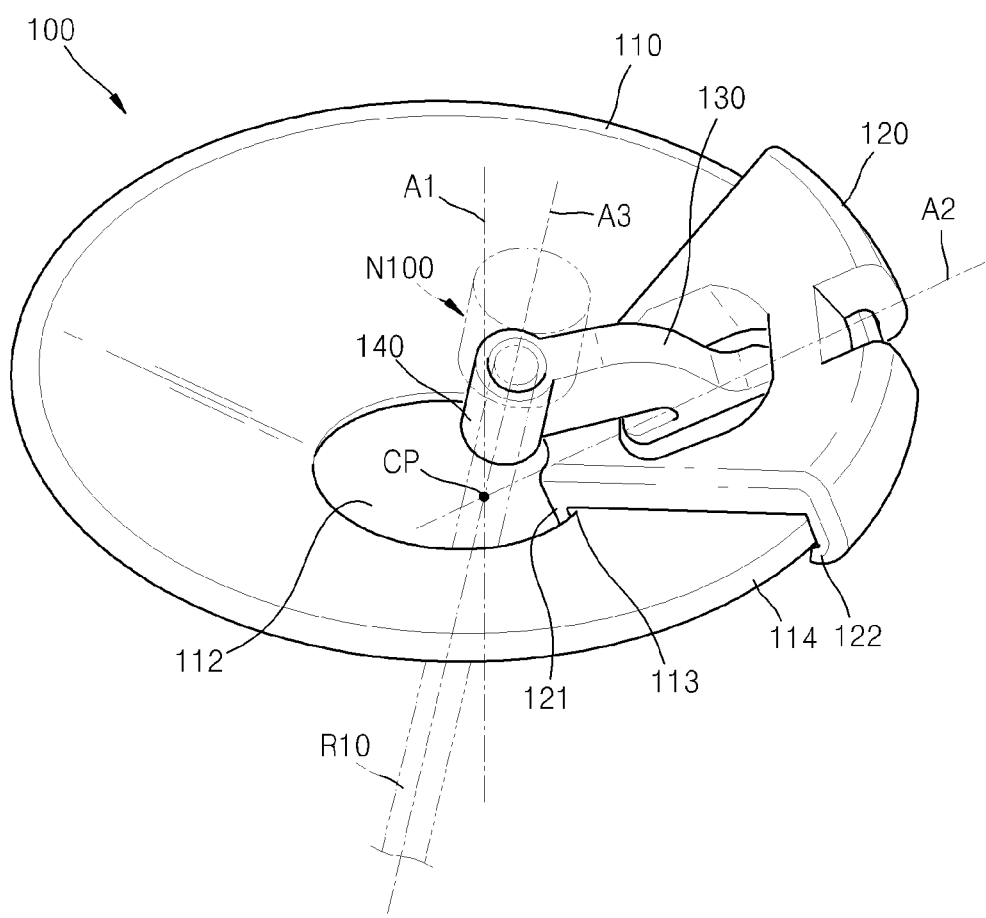
FIG. 3 is a perspective view of a supporter device on which one instrument may be mounted, according to an embodiment of the present invention.

The supporter device 100 supports the instrument N100. FIG. 3 is a perspective view of an example of the supporter device 100. Referring to FIG. 3, the supporter device 100 may include a base member 110, a movable member 120, and a pivot member 130. The base member 110 includes an insertion region 112 through which the instrument N100 passes. The movable member 120 is provided on the base member 110 to be movable around the insertion region 112. The movable member 120 may move along a moving path based on a moveable central axis A1 that penetrates through the insertion region 112. At least a part of the moving path of the movable member 120 is a circle based on the moveable central axis A1. That is, the moving path of the movable member 120 may be a partial circular path or an entire circular path based on the moveable central axis A1. The pivot member 130 is installed on the movable member 120 to be rotatable based on a pivot axis A2. The pivot member 130 includes a mounting portion 140 on which the instrument N100 is mounted. The instrument N100 is mounted on the mounting portion 140 in order for the extension portion R10 to be inserted in the insertion region 112.

Figure 4:
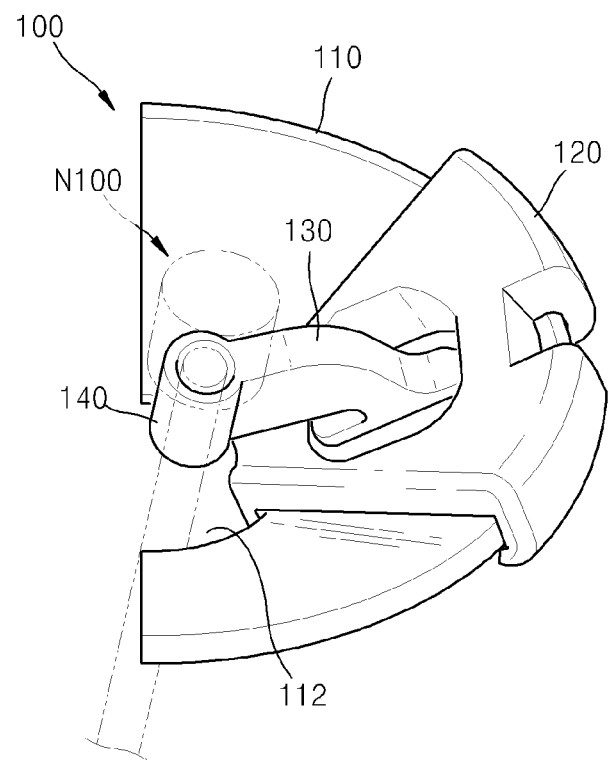
FIG. 4 is a perspective view of a supporter device of a partial conical shape according to another embodiment of the present invention.

The base member 110 may be formed as a conical shape as shown in FIG. 3; however, the present invention is not limited thereto. The base member 110 may be formed as any kind of shape provided that the base member 110 includes the insertion region 112 and may guide the movable member 120 around the insertion region 112, and in the present invention, the base member 110 is not limited to any specific shape. For example, as shown in FIG. 4, the base member 110 may have a partial conical shape. A surgical operation may require two or more instruments N100. In order to reduce the number of times the instrument N100 is replaced during a surgical operation or to not perform a replacement operation at all, two or more supporter devices 100 may be used. In this case, in order to reduce the number of incision ports 30, two or more supporter devices 100 may be disposed with respect to one incision port 30. In addition, in some cases, one or more supporter devices 100 may be disposed with respect to a plurality of incision ports 30 that are adjacent to each other. In this case, the plurality of supporter devices 100 may be effectively disposed to access one incision port 30 by using the conical or partial conical base member 110. In addition, the plurality of supporter devices 100 corresponding to the plurality of incision ports 30 that are adjacent to each other may be effectively arranged. The movable member 120 may be installed so as to be movable along an inner side surface of the base member 110 having a conical shape or a partial conical shape. Although not shown in the drawings, the base member 110 may be formed as a disc shape or a partial disc shape, in which the insertion region 112 is formed on a central portion.

Figure 5:
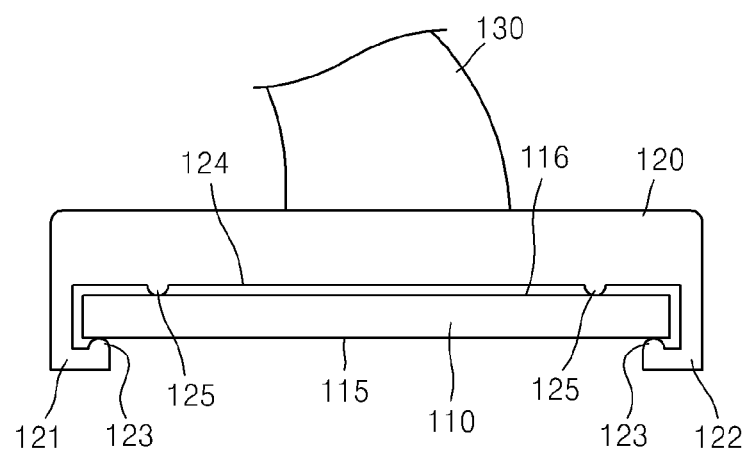
FIG. 5 is a diagram showing an example of a coupling structure between a base member and a movable member.

FIG. 5 is a diagram showing an example of a coupling structure between the movable member 120 and the base member 110. Referring to FIGS. 3 and 5, the movable member 120 may be installed, for example, moveable on the base member 110 by grip portions 121 and 122 that respectively surround an inner edge 113 (e.g., a lip or rim) of the insertion region 112 and an outer edge 114 (e.g., a lip or rim) of the base member 110. The grip portions 121 and 122 may include contact protrusions 123 for reducing friction with a lower surface 115 of the base member 110. In addition, a contact protrusion 125 for reducing friction with an upper surface 116 of the base member 110 may be disposed on a lower surface 124 of the movable member 120. Alternatively, the contact protrusions 123 and 125 may be respectively disposed on the lower surface 115 and the upper surface 116 of the base member 110. Frictional resistance caused by movement of the movable member 120 may be reduced by adopting a roller instead of the contact protrusions 123 and 125. Although not shown in FIG. 5, the movable member 120 may slide along a rail disposed on the base member 110, and other structures may be adopted.

Figure 6:
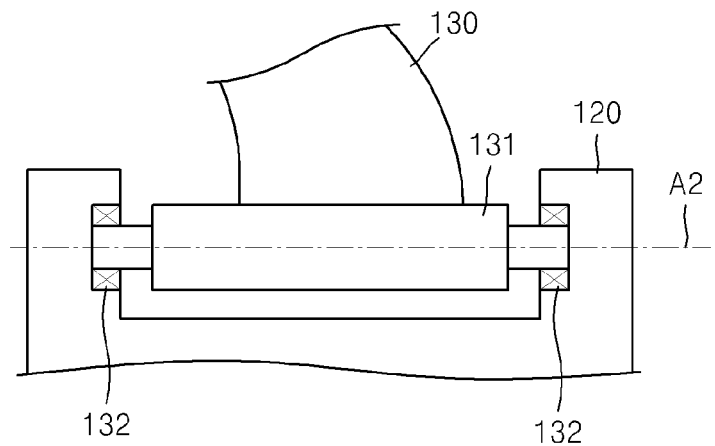
FIG. 6 is a diagram showing an example of a coupling structure between a movable member and a pivot member.

FIG. 6 is a diagram showing an example of a coupling structure between the pivot member 130 and the movable member 120. Referring to FIG. 6, a rotary shaft 131 functioning as the pivot axis A2 is disposed on the pivot member 130. The rotary shaft 131 may be rotatably supported by the movable member 120 via one or more bearings 132.

Figure 7:
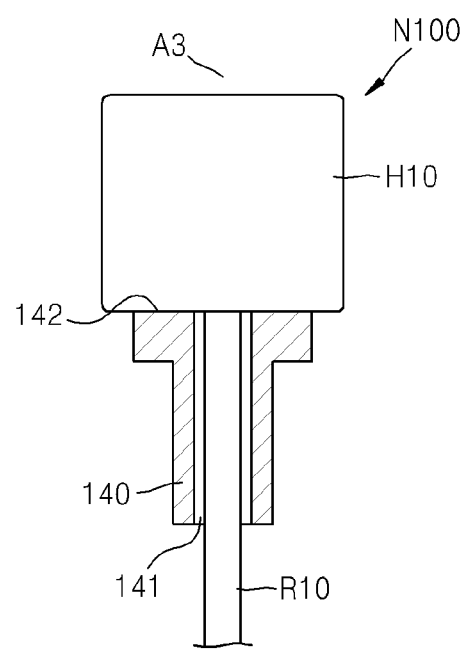
FIG. 7 is a diagram showing an example of a mounting portion on which an instrument is mounted.

FIG. 7 is a cross-sectional view of the mounting portion 140 on which the instrument N100 is mounted. Referring to FIGS. 3 and 7, the mounting portion 140 may include a hollow portion 141 through which, for example, the extension portion R10 of the instrument N100 may pass. A diameter of the hollow portion 141 may be greater than a diameter of the extension portion R10 of the instrument N100. The head portion H10 of the instrument N100 may be supported by an upper surface of the mounting portion 140. The head portion H10 may have a diameter greater than a diameter of the upper portion of the mounting portion 140 which supports the head portion H10. Alternatively, the head portion H10 may have a diameter equal to or less than the diameter of the upper portion of the mounting portion 140 which supports the head portion H10. Although not shown in FIGS. 3 and 7, the mounting portion 140 may include a fixing device for fixing the instrument N100. The fixing device may be coupled to the head portion H10 to fix the instrument N100 on the mounting portion 140.

Figure 8:
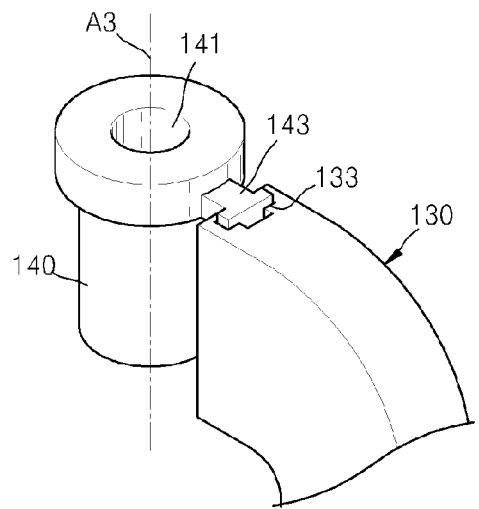
FIG. 8 is a perspective view of a structure for coupling a mounting portion to a pivot member to be elevated.

The instrument N100 may be installed on the pivot member 130 in such a way that the instrument N100 may be elevated in a lengthwise direction thereof, that is, a direction of an extension axis A3. FIG. 8 is a perspective view showing the mounting portion 140 elevated in the extension axis A3 direction. Referring to FIG. 8, the pivot member 130 includes a guide recess 133 cut in a direction of the extension axis A3, and the mounting portion 140 may include a guide protrusion 143 that is inserted in the guide recess 133. According to the above configuration, the mounting portion 140 is elevated along the guide recess 133 in a state where the instrument N100 is mounted on the mounting portion 140, and thus the instrument N100 may be elevated in the direction of the extension axis A3.

The supporter device 100 may further include a driving unit for moving the instrument N100. The driving unit may include one or more motors. The driving unit may be connected to the control station 2 via, for example, by a wired or wireless connection, or a combination thereof. For example, the driving unit may be connected to the control station 2 via an electric control cable (not shown). The driving unit may include a first driving unit (210, refer to FIG. 9A) for driving the movable member 120 and a second driving unit (220, refer to FIG. 9A) for driving the pivot member 130.

Figure 9A:
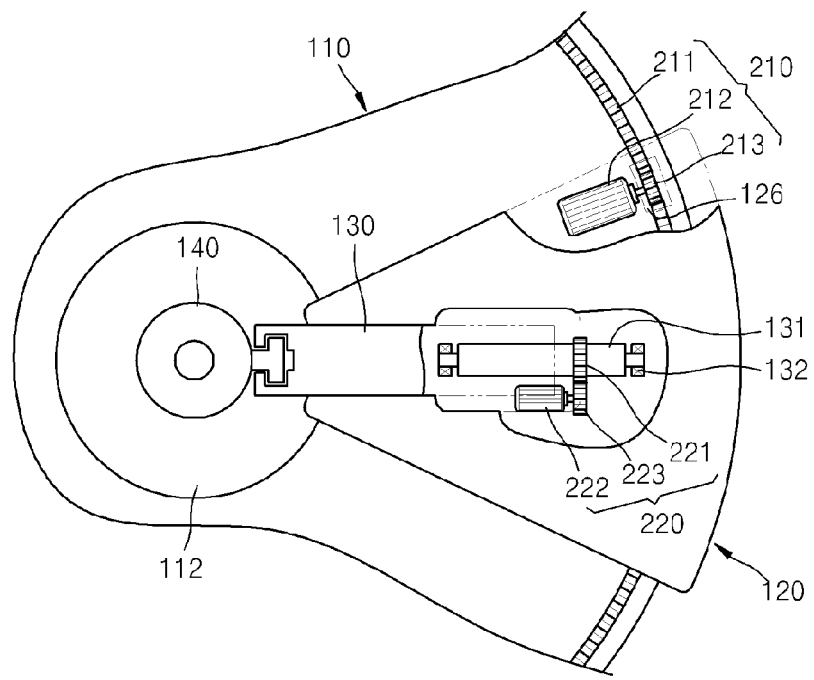
FIG. 9A is a diagram showing an example of a first driving unit for driving a movable member and a second driving unit for driving a pivot member.

FIG. 9A shows an example of the first driving unit 210 and the second driving unit 220. Referring to FIG. 9A, the first driving unit 210 may have a rack-pinion structure. A first driving motor 212 is mounted on the movable member 120. A pinion 213 is coupled to the first driving motor 212. A rack 211 is disposed on the base member 110. The rack 211 is formed on the base member 110 in a circumferential direction based on the movable central axis A1. The movable member 120 includes an opening 126. The pinion 213 located on a lower portion of the movable member 120 is exposed through the opening 126. The pinion 213 is engaged with the rack 211 through the opening 126. According to the above structure, the pinion 213 is rotated by driving the first driving motor 212 so that the movable member 120 may be moved around the insertion region 112. That is, the movable member 120 may be moved around the insertion region 112 along a circular moving path based on the movable central axis A1.

The first driving unit 210 is not limited to the example shown in FIG. 9A. For example, although not shown in FIG. 9A, a linear motor may be adopted as the first driving unit 210. That is, a rail formed of a coil may be arranged on the base member 110 along the circular moving path, and a magnet may be disposed on the movable member 120, and thus the movable member 120 may move along the rail by an electromagnetic repulsive force between the coil and the magnet.

The second driving unit 220 may include a gear portion 221 disposed on the rotary shaft 131 of the pivot member 130, a second driving motor 222 mounted on the movable member 120, and a gear 223 rotated by the second driving motor 222. As described above with reference to FIG. 6, since the rotary shaft 131 is rotatably supported by the movable member 120, the pivot member 130 may be pivoted based on the pivot axis A2 by rotating the second driving motor 222.

Figure 9B:
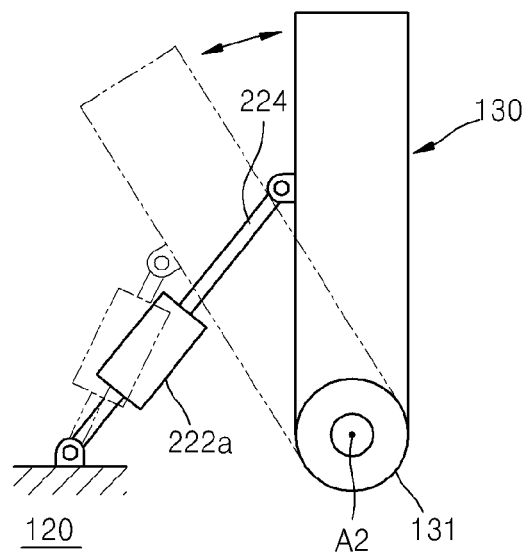
FIG. 9B is a diagram showing another example of a second driving unit for driving a pivot member.

Examples of the second driving unit 220 are not limited to the example shown in FIG. 9A. For example, although not shown in drawings, pulleys may be respectively formed on the rotary shaft 131 and the second driving motor 222, instead of the gear portion 221 and the gear 223, and the pulleys may be connected to each other by using a belt (not shown). Thus, the belt may be driven by using the second driving motor 222, and the pivot member 130 may be pivoted based on the pivot axis A2. In addition, as shown in FIG. 9B, the second driving unit 220 may have a configuration in which an end portion of a driving rod 224 of a linear motor 222a is connected to the movable member 120, and another end of the driving rod 224 is connected to a position separated from the rotary shaft 131 of the pivot member 130. The driving rod 224 is reciprocated by using the linear motor 222a, thereby pivoting the pivot member 130 based on the pivot axis A2.

Figure 10A:
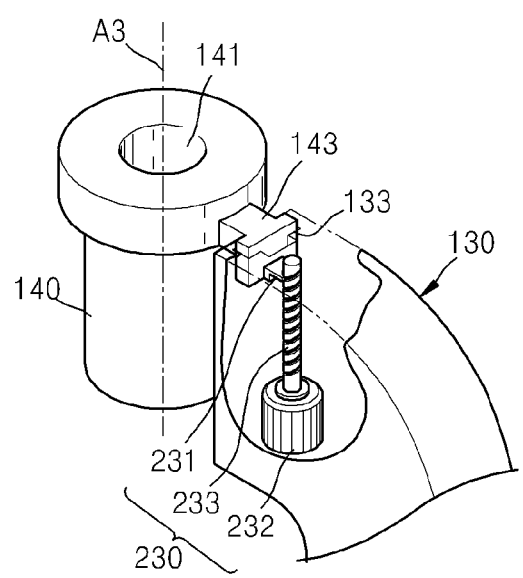
FIG. 10A is a diagram showing an example of a third driving unit for elevating a mounting portion.

The driving unit may further include a third driving unit (230, refer to FIG. 10A) for elevating the mounting portion 140 in the direction of the extension axis A3. FIG. 10A shows the third driving unit 230 according to an embodiment of the present invention. Referring to FIG. 10A, a third driving motor 232 is mounted on the pivot member 130. The third driving motor 232 includes a screw 233 (e.g., a lead screw). The guide protrusion 143 of the mounting portion 140 includes a coupling protrusion 231 coupled to a screw recess of the lead screw 233. According to the above structure, when the lead screw 233 is rotated by the third driving motor 232, the mounting portion 240 may be elevated in the extension axis A3 direction along the screw recess of the lead screw 233.

Figure 10B:
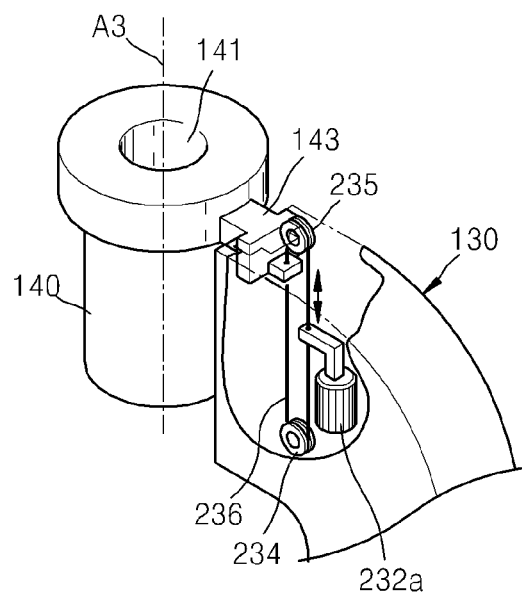
FIG. 10B is a diagram showing another example of a third driving unit for elevating a mounting portion.

The third driving unit 230 is not limited to the example shown in FIG. 10A. For example, as shown in FIG. 10B, the mounting portion 140 is connected to a belt or wire 236 that is supported by a pair of pulleys 234 and 235, and the belt or wire 236 is driven by using a linear motor 232a to elevate the mounting portion 140 in the extension axis A3 direction.

The supporter device 100 may serve as a remote center of motion (RCM) structure for providing the instrument N100 with motion displacement based on a RCM. That is, the instrument N100 is moved by the supporter device 100 based on the RCM as a stationary point. In this point of view, the supporter device 100 provides the instrument N100 with a motion based on the RCM, that is, RCM movement.

Figure 11:
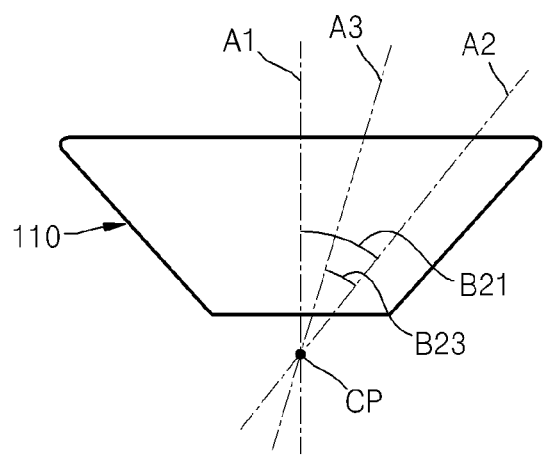
FIG. 11 is a diagram showing a remote center of motion (RCM) realized by the supporter device of FIG. 3, according to an embodiment of the present invention.

Referring to FIG. 11, the movable central axis A1 of the movable member 120, the pivot axis A2 of the pivot member 130, and the extension axis A3 of the instrument N100 mounted on the pivot member 130 cross at a single point CP. The crossed point CP is the RCM. According to the above structure, by moving and pivoting the movable member 120 and the pivot member 130, the supporter device 100 capable of moving the instrument N100 with two degrees of freedom based on the crossed point CP as the stationary point may be realized. In addition, as described above, by elevating the mounting portion 140 in the direction of the extension axis A3, the supporter device 100 capable of moving the instrument N100 with three degrees of freedom based on the crossed point CP as the stationary point may be realized.

Figure 12:
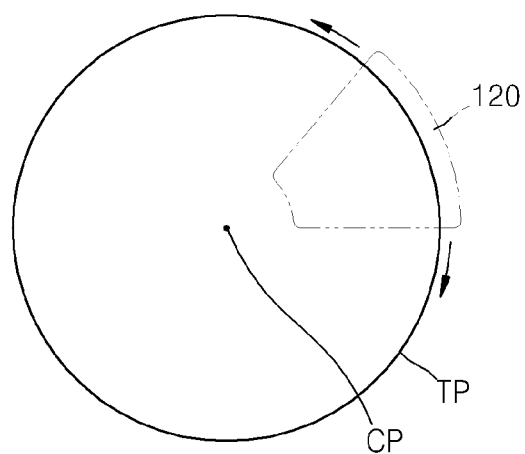
FIG. 12 is a diagram showing a traveling path of a movable member in the supporter device of FIG. 3.

Referring to FIG. 12, the movable member 120 may be moved along a traveling path TP formed as an arc. The traveling path TP may have a complete circular shape, or may have a partial arc shape. If the base member 110 is formed as a partial conical shape or a partial disc shape, the traveling path TP is formed as a partial arc shape.

Figure 13:
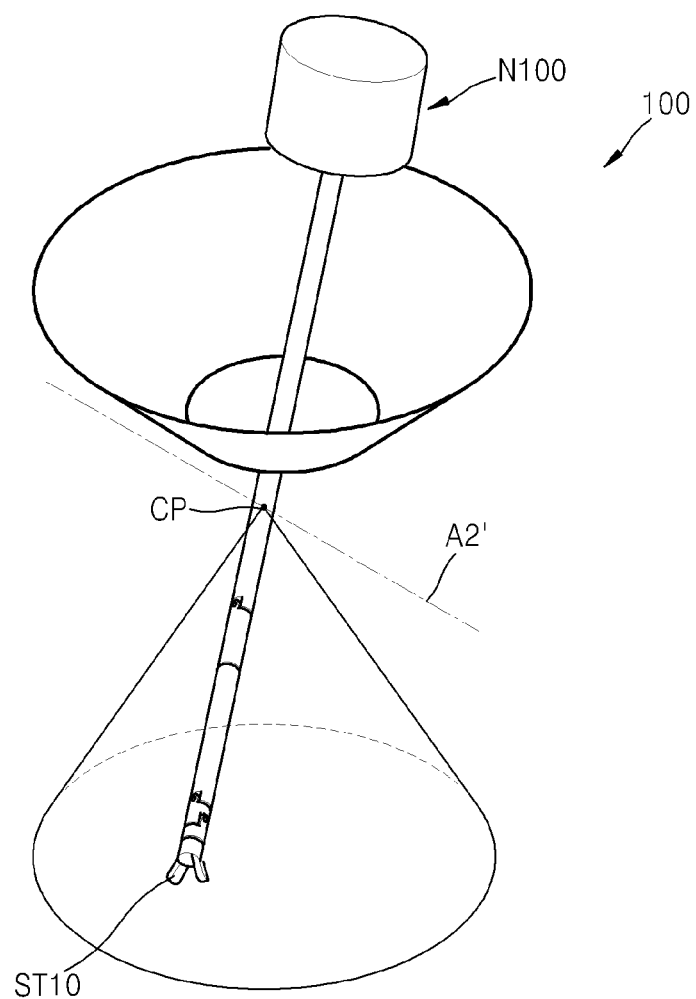
FIG. 13 is a diagram showing a workspace of an instrument mounted on the supporter device of FIG. 3.

A moving trace of the instrument N100 according to movement of the movable member 120 and pivoting of the pivot member 130 is a conical shape having the crossed point CP as an apex as shown in FIG. 13, and an inner space of the conical shape is a workspace in which the surgical tool ST10 may access a diseased part. The crossed point CP may be located at the incision port 30, or may be located on an outer or inner side of the incision port 30. As the crossed point CP approaches the incision port 30, a size of the incision port 30 may be reduced while ensuring a relatively large workspace.

According to a conventional robot surgery system, the instrument N100 is mounted on each of a plurality of multi-joint robot arms. Therefore, in order to move each of the instruments N100, a robot arm that is complicated and has a plurality of joints is necessary. In addition, a plurality of robot arms have to move the plurality of instruments N100 inserted in one incision port 30 or a plurality of the incision ports 30 adjacent to each other, and during this operation, the multi-joint robot arms may interfere with each other and it is difficult to ensure a relatively large workspace for each of the instruments N100. On the other hand, the supporter device 100 of the present embodiment may move the instrument N100 based on the crossed point CP, that is, the RCM, in a state of being fixed at a certain position. A space necessary for moving the instrument N100 is limited to a space occupied by the supporter device 100 itself. Therefore, the workspace of the instrument N100 may be ensured without interference between the supporter devices 100. Also, by adopting the instrument N100 having a multi-joint structure that will be described later, operations involving a high degree of freedom may be performed.

According to the supporter device 100 of the present embodiment, the pivot axis A2 passes through the insertion region 112. That is, the pivot axis A2 extends from inside the base member 110 to outside the base member 110, passes through the insertion region 112, and crosses the movable central axis A1 at the crossed point CP, or at least an extension line of the pivot axis A2 passes through the insertion region 112. That is, for example, the pivot axis A2 may extend from inside the base member 110 to outside the base member 110, pass through the insertion region 112, and cross the movable central axis A1 at the crossed point CP, into the workspace which is the inner space of the conical shape having the crossed point CP as an apex as shown in FIG. 13. If the pivot axis A2 or the extension line of the pivot axis A2 does not pass through the insertion region 112, for example, a pivot axis A2' shown in FIG. 13, the pivot member 130 has to be supported by the movable member 120 to be moved along an arc-shaped path based on the pivot axis A2'. Therefore, a coupling structure between the pivot member 130 and the movable member 120 may be complicated. According to the supporter device 100 of the present embodiment, in which the pivot axis A2 passes through the insertion region 112, the pivot member 130 may be supported by the movable member 120 to be pivoted according to a simple structure, in which the rotary shaft 131 functioning as the pivot axis A2 is supported by the movable member 120.

Referring to FIG. 11, when the supporter device 100 supports one instrument N100, that is, when the supporter device 100 includes one movable member 120 and one pivot member 130, the extension axis A3 may have any angular position, provided that the extension axis A3 passes through the crossed point CP. That is, based on a state where the extension axis A3 is located in the plane including the movable central axis A1 and the pivot axis A2, the extension axis A3 may be located between the movable central axis A1 and the pivot axis A2, may coincide with the movable central axis A1, or may be located at a side opposite to the pivot axis A2 based on the movable central axis A1.

However, it is advantageous that an angle B23 formed by the pivot axis A2 and the extension axis A3 be small, in order to reduce a load on the second driving motor 222 for driving the pivot member 130. Considering this, based on a state where the extension axis A3 is located in the plane including the movable central axis A1 and the pivot axis A2, the angle B23 formed by the pivot axis A2 and the extension axis A3 may be equal to or less than an angle B21 formed by the pivot axis A2 and the movable central axis A1. That is, the extension axis A3 may be located between the pivot axis A2 and the movable central axis A1.

Figure 14:
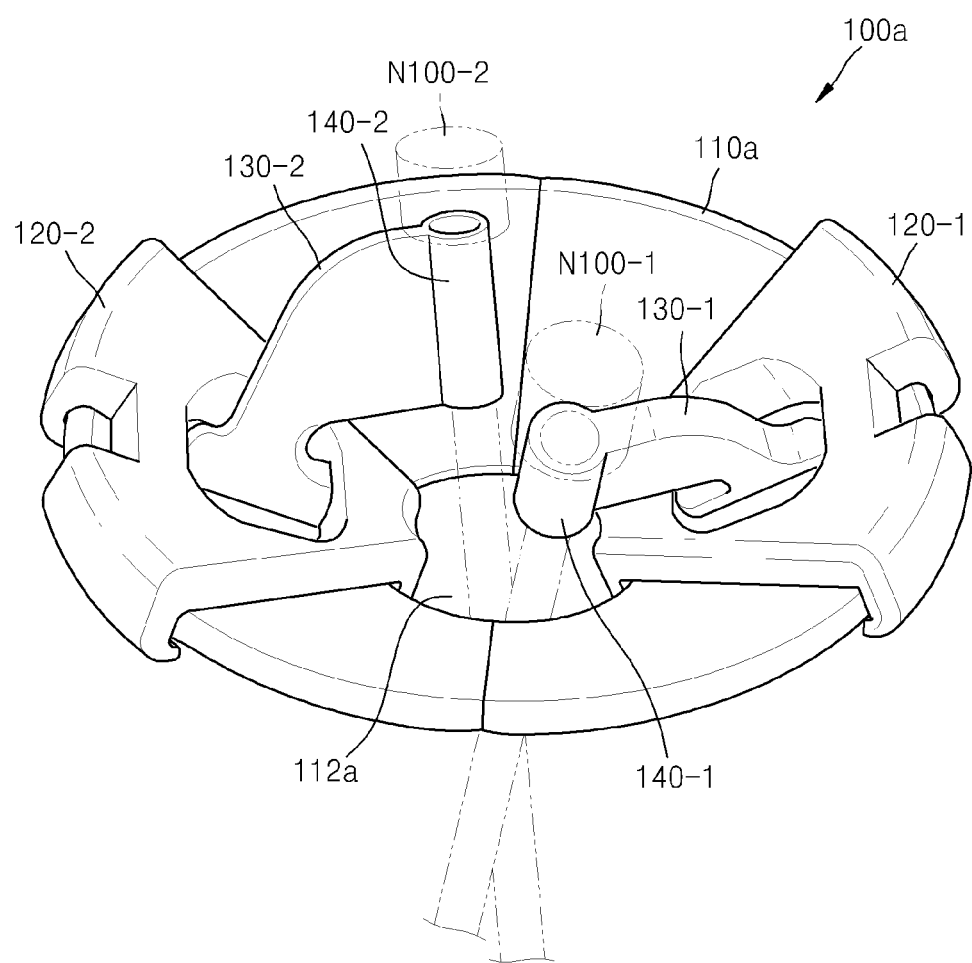
FIG. 14 is a perspective view of a supporter device on which two instruments may be mounted, according to another embodiment of the present invention.

In the above embodiment, the supporter device 100 for supporting one instrument N100 is described; however, the present invention is not limited thereto. FIG. 14 shows a supporter device 100a for supporting two instruments N100-1 and N100-2 according to another embodiment of the present invention.

Referring to FIG. 14, a base member 110a, first and second movable members 120-1 and 120-2, and first and second pivot members 130-1 and 130-2 are shown. The first and second movable members 120-1 and 120-2 are installed to be movable around an insertion region 112a formed in the base member 110a. The first and second pivot members 130-1 and 130-2 are respectively coupled to the first and second movable members 120-1 and 120-2 to be pivotable. The first and second pivot members 130-1 and 130-2 respectively include first and second mounting portions 140-1 and 140-2. The first and second instruments N100-1 and N100-2 are respectively mounted on the first and second mounting portions 140-1 and 140-2. The first and second mounting portions 140-1 and 140-2 may be coupled to the first and second pivot members 130-1 and 130-2 to be elevated in length directions of the first and second instruments N100-1 and N100-2.

The base member 110a may be formed as a conical shape as shown in FIG. 14; however, the present invention is not limited thereto. The base member 110a may have any kind of shape, provided that the base member 110a includes the insertion region 112a and may guide the first and second movable members 120-1 and 120-2 around the insertion region 112a, and in the present invention, the base member 110a is not limited to any specific shape. For example, the base member 110a may have a partial conical shape, or may be formed as a disc or a partial disc shape, having a center portion where the insertion region 112a is formed.

A structure for coupling the first and second movable members 120-1 and 120-2 to the base member 110a may be the same as that of FIG. 5. In addition, a structure of a driving unit for moving the first and second movable members 120-1 and 120-2 may be the same as that of the first driving unit 210 shown in FIG. 9A. Coupling structures between the first and second pivot members 130-1 and 130-2 and the first and second movable members 120-1 and 120-2 may be the same as the coupling structure shown in FIG. 6. In addition, a structure of a driving unit for moving the first and second pivot members 130-1 and 130-2 may be the same as that of the second driving unit 220 shown in FIG. 9A or FIG. 9B. Coupling structures of the first and second mounting portions 140-1 and 140-2 and the first and second pivot members 130-1 and 130-2 may be the same as the coupling structure shown in FIG. 7 or FIG. 8. A structure of a driving unit for elevating the first and second mounting portions 140-1 and 140-2 may be the same as that of the third driving unit 230 shown in FIG. 10A or FIG. 10B.

Figure 15:
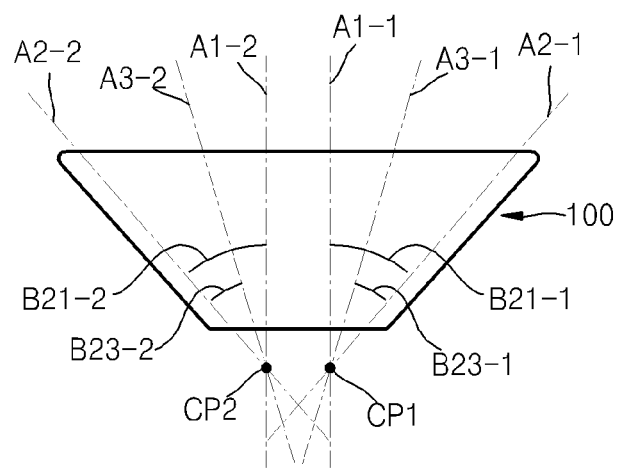
FIG. 15 is a diagram showing RCMs realized by the supporter device of FIG. 14.

As shown in FIG. 15, a movable central axis (hereinafter, a first movable central axis A1-1) of the first movable member 120-1, a pivot axis (hereinafter, a first pivot axis A2-1) of the first pivot member 130-1, and an extension axis (hereinafter, a first extension axis A3-1) of the first instrument N100-1 mounted on the first pivot member 130-1 cross at a single point CP-1. In addition, a movable central axis (hereinafter, a second movable central axis A1-2) of the second movable member 120-2, a pivot axis (hereinafter, a second pivot axis A2-2) of the second pivot member 130-2, and an extension axis (hereinafter, a second extension axis A3-2) of the second instrument N100-2 mounted on the second pivot member 130-2 cross at a single point CP-2. The first crossed point CP-1 and the second crossed point CP-2 respectively are RCMs of the first and second instruments N100-1 and N100-2. The first and second crossed points CP-1 and CP-2 may be separated from each other. A distance between the first and second crossed points CP-1 and CP-2 may be at least greater than one of the diameters of respective extension portions R10 of the first and second instruments N100-1 and N100-2 in order to prevent interference between the first and second instruments N100-1 and N100-2, noting that diameters of the respective extension portions R10 may be different from one another.

According to the above structure, by moving the first and second movable members 120-1 and 120-2 and pivoting the first and second pivot members 130-1 and 130-2, the first and second instruments N100-1 and N100-2 may be moved based on the first and second crossed points CP-1 and CP-2 as stationary points. Therefore, the supporter device 100a capable of moving each of the first and second instruments N100-1 and N100-2 with two degrees of freedom based on the RCMs may be realized. In addition, as described above, by elevating the first and second mounting portions 140-1 and 140-2, the supporter device 100a may be capable of moving each of the first and second instruments N100-1 and N100-2 with three degrees of freedom.

According to the supporter device 100a of the present embodiment, the first and second pivot axes A2-1 and A2-2 pass through the insertion region 112a. That is, the first and second pivot axes A2-1 and A2-2 or extension lines thereof extend from inside the base member 110a to outside the base member 110a and pass through the insertion region 112a. According to the above structure, the first and second pivot members 130-1 and 130-2 may be supported by the first and second movable members 120-1 and 120-2 to be pivotable in the simple structure shown in FIG. 6.

Figure 16:
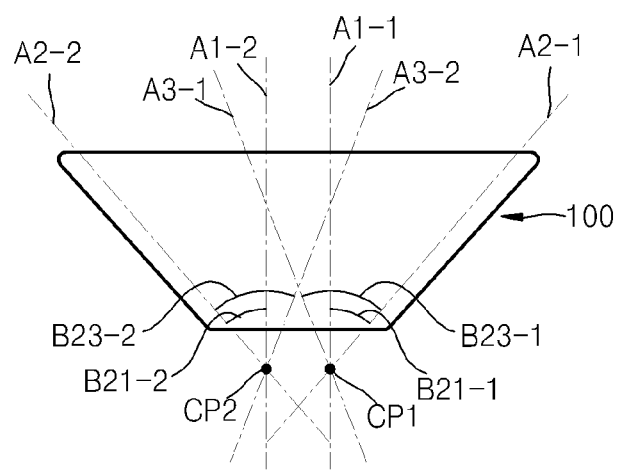
FIG. 16 is a diagram showing locations of extension axes of a first instrument and a second instrument.

As shown in FIG. 16, based on a state where the first and second extension axes A3-1 and A3-2 are located within the plane including the first and second pivot axes A2-1 and A2-2 and the first and second movable central axes A1-1 and A1-2, if angles B23-1 and B23-2 formed respectively by the first and second pivot axes A2-1 and A2-2 and the first and second extension axes A3-1 and A3-2 are greater than angles B21-1 and B21-2 formed by the first and second pivot axes A2-1 and A2-2 and the first and second movable central axes A1-1 and A1-2, the first and second extension axes A3-1 and A3-2 cross each other. For example, as can be seen from FIG. 16, A3-1 and A3-2 cross one another (intersect) at a point which corresponds to a point inside the base member 110 and which is above CP1 and CP2, and which is also above the insertion region. Thus, the first and second instruments N100-1 and N100-2 interfere with each other, thereby restricting workspaces of the first and second instruments N100-1 and N100-2. Therefore, according to the supporter device 100a of the present embodiment, as shown in FIG. 15, based on a state where the first extension axis A3-1 is located within the plane including the first pivot axis A2-1 and the first movable central axis A1-1, the first extension axis A3-1 may be located between the first movable central axis A1-1 and the pivot axis A2-1, or may coincide with the first movable central axis A1-1. That is, the angle B23-1 formed by the first pivot axis A2-1 and the first extension axis A3-1 may be equal to or less than the angle B21-1 formed by the first pivot axis A2-1 and the first movable central axis A1-1. Likewise, based on a state where the second extension axis A3-2 is located within the plane including the second pivot axis A2-2 and the second movable central axis A1-2, the second extension axis A3-2 may be located between the second movable central axis A1-2 and the second pivot axis A2-2, or may coincide with the second movable central axis A1-2. The angle B23-2 formed by the second pivot axis A2-2 and the second extension axis A3-2 may be equal to or less than the angle B21-2 formed by the second pivot axis A2-2 and the second movable central axis A1-2. According to the above structure, the workspaces of the first and second instruments N100-1 and N100-2 may be increased while minimizing interference between the first and second instruments N100-1 and N100-2. In addition, by reducing the angles B23-1 and B23-2 formed by the first and second pivot axes A2-1 and A2-2 and the first and second extension axes A3-1 and A3-2, a driving load on driving motors for pivoting the first and second pivot members 130-1 and 130-2 may be reduced.

Figure 17:
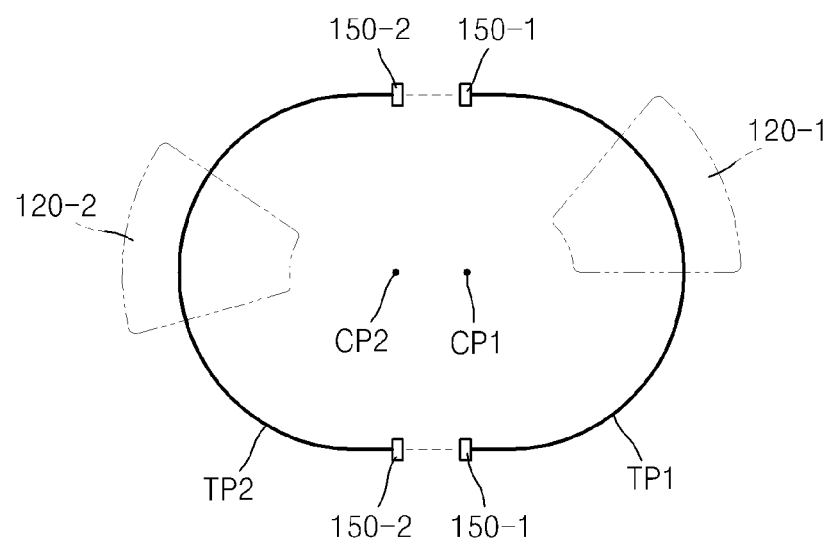
FIG. 17 is a diagram showing traveling paths of first and second movable members in the supporter device of FIG. 14.

Referring to FIG. 17, the first movable member 120-1 may move along a first traveling path TP-1 formed as an arc based on the first crossed point CP1. The second movable member 120-2 may move along a second traveling path TP-2 formed as an arc based on the second crossed point CP-2. The first and second traveling paths TP-1 and TP-2 are not necessarily formed as complete arc shapes. In addition, both of the first and second movable members 120-1 and 120-2 may be moved 360° along the first and second traveling paths TP-1 and TP-2. In this case, locations of the first crossed point CP-1 and the second crossed point CP-2 are changed with respect to each other, and the first and second instruments N100-1 and N100-2 are moved respectively based on the second and first crossed points CP-2 and CP-1 as the RCMs. For example, when the first movable member 120-1 enters the second traveling path TP-2, the RCM of the first instrument N100-1 becomes the second crossed point CP-2. However, when both of the first and second movable members 120-1 and 120-2 are located on the first traveling path TP-1 or the second traveling path TP-2, the RCMs of the first and second instruments N100-1 and N100-2 become the same, and thus, the first and second instruments N100-1 and N100-2 interfere with each other. To address the above problem, movable ranges of the first and second movable members 120-1 and 120-2 may be respectively limited to the first and second traveling paths TP-1 and TP-2. The supporter device 100a may further include first and second blocking portions 150-1 and 150-2 that respectively block the first and second movable members 120-1 and 120-2 from respectively entering the second and first traveling paths TP-2 and TP-1. As an example, the first and second blocking portions 150-1 and 150-2 may be protrusions that protrude from the base member 110a to contact the first and second movable members 120-1 and 120-2 and that are located opposite on end portions of the first and second traveling paths TP-1 and TP-2. The first and second blocking portions 150-1 and 150-2 may be detachable such that the first and second movable members 120-1 and 120-2 may be freely moved about each of the travelling paths, for example, to switch positions of the moveable members. For example, the first and second movable members may have different surgical instruments (surgical tools) attached thereto, and it may be desirable to switch positions of the moveable members to access a specific region (workspace) using one of the different surgical instruments. After switching positions of the moveable members, the first and second blocking portions 150-1 and 150-2 may be reattached to prevent interference between the newly positioned movable members.

In another embodiment, when both of the first and second movable members 120-1 and 120-2 are positioned such that the RCMs of the first and second instruments N100-1 and N100-2 become the same or about the same, it may be detected that the first and second instruments N100-1 and N100-2 are about to interfere with each other, or are interfering with one another. Accordingly, an operator may be informed that the first and second instruments N100-1 and N100-2 are about to interfere with each other, or are interfering with one another, by sending a communication from the supporter device 100 to the control station 2. For example, an alarm may be output to the operator at the control station 2, including an alarm sound, an alarm light, display of a warning message, a vibration sent to the operator via the joystick or manipulation unit, flickering of an icon, or the like.

Figure 18:
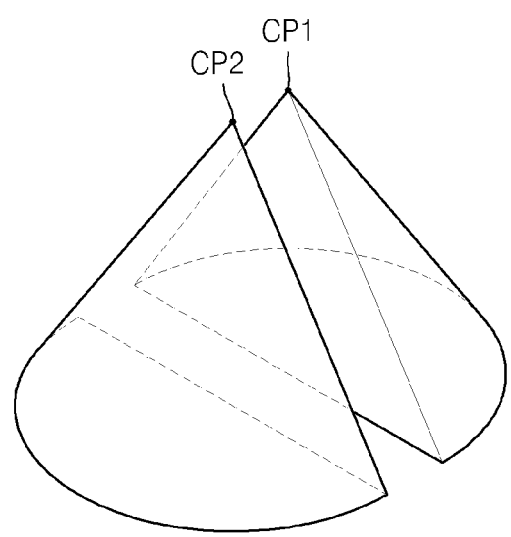
FIG. 18 is a diagram showing workspaces of first and second instruments mounted on the supporter device of FIG. 14.

Moving traces of the first and second instruments N100-1 and N100-2 formed by the supporter device 100a are formed as semi-conical shapes having the first and second crossed points CP-1 and CP-2 as apexes, as shown in FIG. 18. In addition, inner spaces of the two semi-conical shapes become workspaces in which surgical tools ST10 of the first and second instruments N100-1 and N100-2 access diseased parts. The first and second crossed point CP-1 and CP-2 may be located at an incision port 30, or may be located on an outer or inner side of the incision port 30. By forming the first and second crossed points CP-1 and CP-2 adjacent to the incision port 30, a size of the incision port 30 may be reduced while ensuring a relatively large workspace.

In a conventional robot surgery system in which an instrument is mounted on each of a plurality of multi-joint robot arms, the multi-joint robot arms interfere with each other during moving of instruments, and thus it is not easy to ensure the a relatively large workspace for each of the instruments and to ensure that the instruments do not interfere with each other. Accordingly, the supporter device 100a of the present embodiment may move the two instruments N100-1 and N100-2 based on the RCMs separated from each other in a state where the supporter device 100a is located at a fixed position. A space for moving the instruments N100-1 and N100-2 may be limited to a space occupied by the supporter device 100a. In addition, the first and second movable members 120-1 and 120-2 and the first and second pivot members 130-1 and 130-2 are independently moved within restricted areas. Therefore, the first and second instruments N100-1 and N100-2 may be moved without interference between the first and second movable members 120-1 and 120-2 and between the first and second pivot members 130-1 and 130-2, and a relatively large workspace for each of the first and second instruments N100-1 and N100-2 may be ensured. In addition, even when a plurality of supporter devices 100a are arranged at one incision port 30, there is no interference between the plurality of supporter devices 100a.

In the above embodiment, the supporter device on which one or two instruments are mounted is described; however, the present invention is not limited thereto. That is, a supporter device on which three or more instruments are mounted with an RCM corresponding to each of the instruments may be realized according to the present invention.

Figure 19:
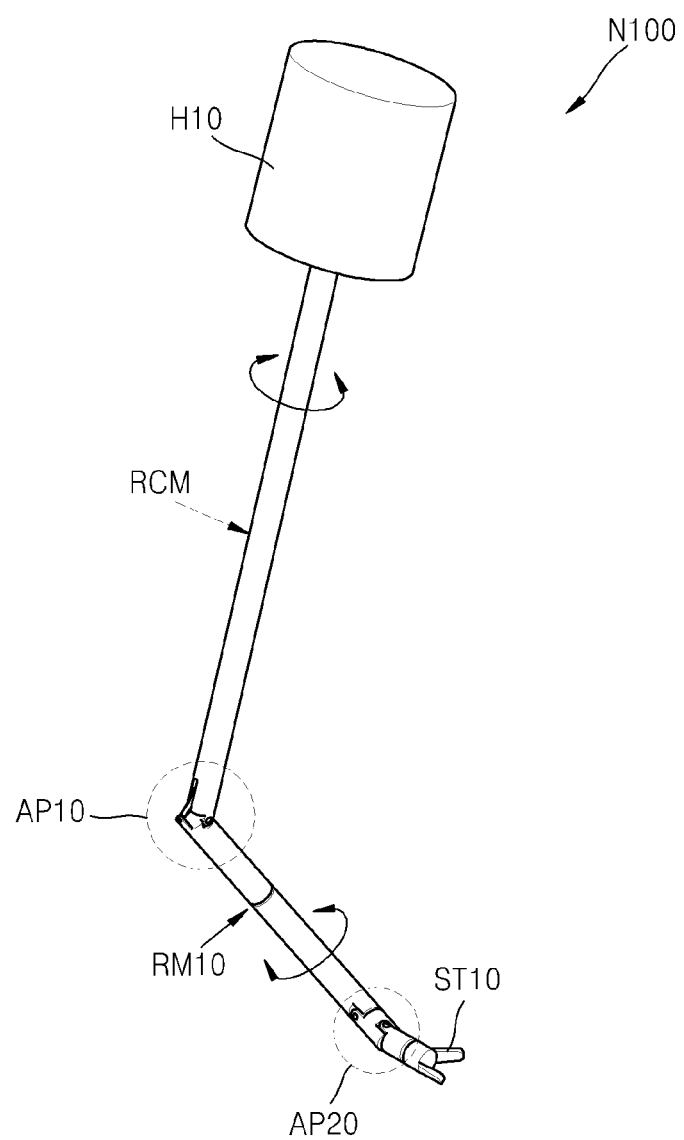
FIG. 19 is a perspective view of a surgical instrument according to another embodiment of the present invention.

FIG. 19 is a perspective view of an instrument N100 for surgery according to another embodiment of the present invention.

Referring to FIG. 19, the surgical instrument (hereinafter, an instrument) N100 according to the present embodiment may have a thin arm shape or other shapes similar to an arm. The instrument N100 may include at least one joint portion, for example, a first joint portion AP10 and a second joint portion AP20. The first and second joint portions AP10 and AP20 may be spaced apart from each other. The first joint portion AP10 may be located between a head portion H10 and the second joint portion AP20 of the instrument N100. The first joint portion AP10 may be located between an RCM point (that is, the stationary point) of the instrument N100 and the second joint portion AP20. The second joint portion AP20 may be located at an end portion (end portion inserted into an object) of the instrument N100 or a portion adjacent to the end portion. When considering locations and functions of the first and second joint portions AP10 and AP20, the first joint portion AP10 may be referred to or analogized to as an elbow, and the second joint portion AP20 may be referred to or analogized to as a wrist. The second joint portion AP20 may be spaced apart about 4 cm or farther from the first joint portion AP10. A predetermined surgical tool ST10 may be connected to (or mounted on) an end portion of the second joint portion AP20. The surgical tool ST10 may be, for example, a needle holder, micro-dissector, staple applier, tacker, suction irrigation tool, clip applier, cutting blade, irrigator, catheter, suction orifice, surgical knife, surgical forceps, scissors, a cautery (a tool for burning or cutting a diseased part by using electric energy or heat energy), endoscope camera, or the like. In FIG. 19, surgical forceps are exemplary shown as the surgical tool ST10.

The first joint portion AP10 may be configured to move with at least one degree of freedom. For example, the first joint portion AP10 may be configured to perform at least a pitch movement. A configuration of the first joint portion AP10 will be described in more detail later with reference to FIGS. 20 through 24. The second joint portion AP20 may be configured to move with at least two degrees of freedom. For example, the second joint portion AP20 may perform a yaw-pitch motion, a pitch-roll motion, a pitch-yaw motion, a yaw-roll motion, a yaw-pitch-roll motion, and a pitch-yaw-roll motion. FIG. 19 shows a case where the second joint portion AP20 may perform the yaw-pitch motion.

Meanwhile, the surgical tool ST10 may be configured to move with at least one degree of freedom. As shown in FIG. 19, if the surgical tool ST10 is a surgical forceps, the surgical tool ST10 may perform at least a grasping motion.

A rotary motion portion RM10 adjacent to the first joint portion AP10 may be further provided. The rotary motion portion RM10 may be disposed between the first joint portion AP10 and the second joint portion AP20. A part of the instrument N100 under the rotary motion portion RM10 may roll due to the rotary motion portion RM10. That is, a lower portion of the instrument N100 including the second joint portion AP20 and the surgical tool ST10 may roll due to the rotary motion portion RM10. A configuration of the rotary motion portion RM10 will be described in more detail later with reference to FIGS. 25 and 26.

A driving unit for controlling movement of the instrument N100 may be disposed in the head portion H10 of the instrument N100. In this point of view, the head portion H10 may be referred to as the driving unit. Thus, the head portion H10 may include a plurality of motors. A plurality of connection elements may be connected to the plurality of motors. The plurality of connection elements may be connected to the first joint portion AP10, the second joint portion AP20, the rotary motion portion RM10, and the surgical tool ST10 inside the instrument N100 from the head portion H10. That is, the head portion H10 may be connected to the first joint portion AP10, the second joint portion AP20, the rotary motion portion RM10, and the surgical tool ST10 via the plurality of connection elements. The head portion H10 may move the first joint portion AP10, the second joint portion AP20, the rotary motion portion RM10, and the surgical tool ST10 by pushing and/or pulling the plurality of connection elements. In addition, the head portion H10 may further include a driving element for rolling a part of the instrument N100 under the head portion H10. In a state where the head portion H10 is fixed by a predetermined fixing element, a part of the instrument N100 under the head portion H10 may be rolled. Rolling of the part of the instrument N100 under the head portion H10 denotes that all of the first joint portion AP10, the second joint portion AP20, and the surgical tool ST10 are rolled together. A configuration of the head portion H10 will be described in more detail later with reference to FIGS. 27 through 29.

Hereinafter, the first joint portion AP10 of FIG. 19 will be described in detail with reference to FIGS. 20 through 23.

Figure 20:
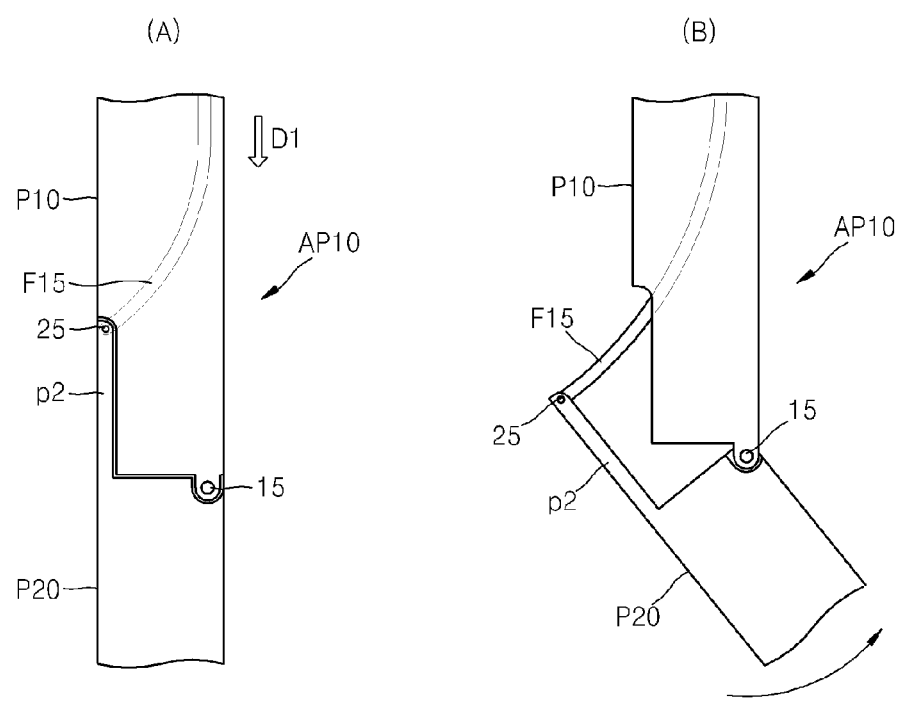
FIG. 20 is a diagram showing a configuration of a first joint portion shown in FIG. 19.

FIG. 20 is a diagram showing the first joint portion AP10 of FIG. 19 in more detail. In FIG. 20, (A) denotes a state where the first joint portion AP10 is not bent, and (B) denotes a state where the first joint portion AP10 is bent.

Referring to (A) of FIG. 20, the first joint portion AP10 may include a first part P10, a second part P20 connected to the first part P10 to be bent (rotated) with respect to the first part P10, and a force applying element F15 connected to the second part P20 to apply a bending (rotating) force to the second part P20. A distance between a first point 15 where the first part P10 and the second part P20 are joined (connected) to each other (hereinafter, a joint point 15) and a second point 25 of the second part P20 to which a force is applied from the force applying element F15 (hereinafter, a force application point 25) may be greater than a diameter of at least one of the first part P10 and the second part P20. That is, the distance between the joint point 15 and the force application point 25 (shortest distance) may be greater than a diameter of the instrument N100 at the first joint portion AP10. For example, the distance between the joint point 15 and the force application point 25 may be at least about 1.5 times, for example, about 1.5 to about 3 times, longer than the diameter of the first part P10 or the second part P20.

In the present embodiment, the force application point 25 may be located toward the first part P10 relative to the joint point 15. That is, the force application point 25 may be located on a portion above the joint point 15 in the drawings. To do this, a protrusion p2 protruding toward the first part P10 may be provided at an end portion of the second part P20, and the force application point 25 may be an end portion of the protrusion p2. That is, the force applying element F15 may be connected to the end portion of the protrusion p2. Meanwhile, the force application point 25 may be located at an outer portion of the second part P20 (left portion in the drawings) based on a bending (rotating) direction of the second part P20, and the joint point 15 may be located at an inner portion of the second part P20 (right portion in the drawings) based on the bending (rotating) direction of the second part P20.

The force applying element F15 may be an elastic body formed of an elastic material. The elastic material may be a superelastic material. For example, the force applying element F15 may be formed of an elastic material such as a shape memory alloy (SMA). The SMA may be, for example, an alloy of Ni—Ti, Cu—Zn, Cu—Zn—Al, Cu—Al—Ni, or the like. When the force applying element F15 is formed of an elastic material, the force applying element F15 may have a curved structure. The force applying element F15 may be flexible, and a degree of curvature of the force applying element F15 may vary depending on a force applied to the force applying element F15. The force applying element F15 may be formed as, for example, a curved rod, or other similar shapes. The force applying element F15 may have a constant (uniform) cross-section, but if necessary, the force applying element F15 may have a non-uniform cross-section so that relatively large deformation may occur at a certain portion. For example, curvature may relatively greatly occur at a portion where the cross-sectional area is reduced.

In (A) of FIG. 20, when the force applying element F15 is pushed in a first direction D1 (lower portion in the drawing), as shown in (B) of FIG. 20, the second part P20 may be bent (rotated) with respect to the first part P10. Since the distance between the joint point 15 and the force application point 25 is greater than the diameter of at least one of the first part P10 and the second part P20, for example, the first part P10, the second part P20 may be easily bent with a relatively small force, like in accordance with a lever principle. That is, when the distance between a fulcrum (joint point 15) and a force point (force application point 25) becomes longer, a relatively large force may be applied to an opposite side to the force point (force application point 25) with respect to the fulcrum (joint point 15). Therefore, the second part P20 may be easily bent (rotated) with a relatively small force, and when the second part P20 is bent (rotated), a relatively strong force may be transferred to the second part P20. Therefore, the instrument N100 including the first joint portion AP10 may perform a surgery operation with a relatively strong force.

Although not shown in FIG. 20, a plurality of wires (or cables) passing inside the first joint portion AP10 may be further provided. The plurality of wires may be connected to the rotary motion portion RM10, the second joint portion AP20, and the surgical tool ST10 from the head portion H10 of FIG. 19 to be used to drive motions of the rotary motion portion RM10, the second joint portion AP20, and the surgical tool ST10.

Figure 21:
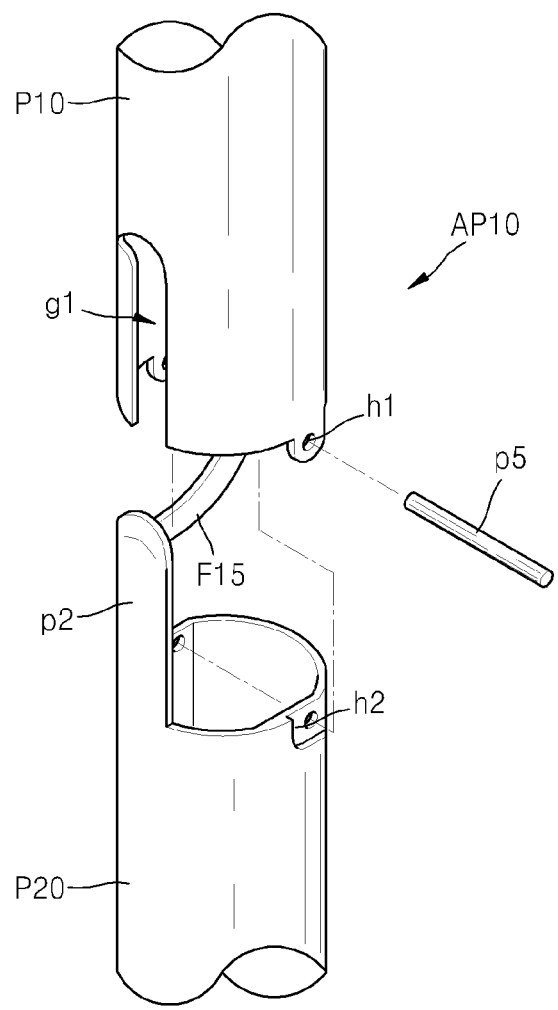
FIG. 21 is an exploded perspective view of a first bending portion of FIG. 20.

FIG. 21 is an exploded perspective view of the first joint portion AP10 of FIG. 20.

Referring to FIG. 21, the protrusion p2 protruding toward the first part P10 may be formed at the end portion of the second part P20, and a groove g1 for receiving the protrusion p2 may be formed in the first part P10. The force applying element F15 may be connected to the end portion of the protrusion p2. The force applying element F15 may be inserted in the first part P10. The first part P10 and the second part P20 may be connected to each other by, for example, a joint pin p5. A first insertion hole h1 and a second insertion hole h2 to which the joint pin p5 is inserted may be formed at end portions of the first part P10 and the second part P20. The end portion of the first part P10 in which the first insertion hole h1 is formed and the end portion of the second part P20 in which the second insertion hole h2 is formed may be inserted into each other. However, the structure shown in FIG. 21 is an example, and the structure of the first joint portion AP10 may be variously modified.

Figure 22:
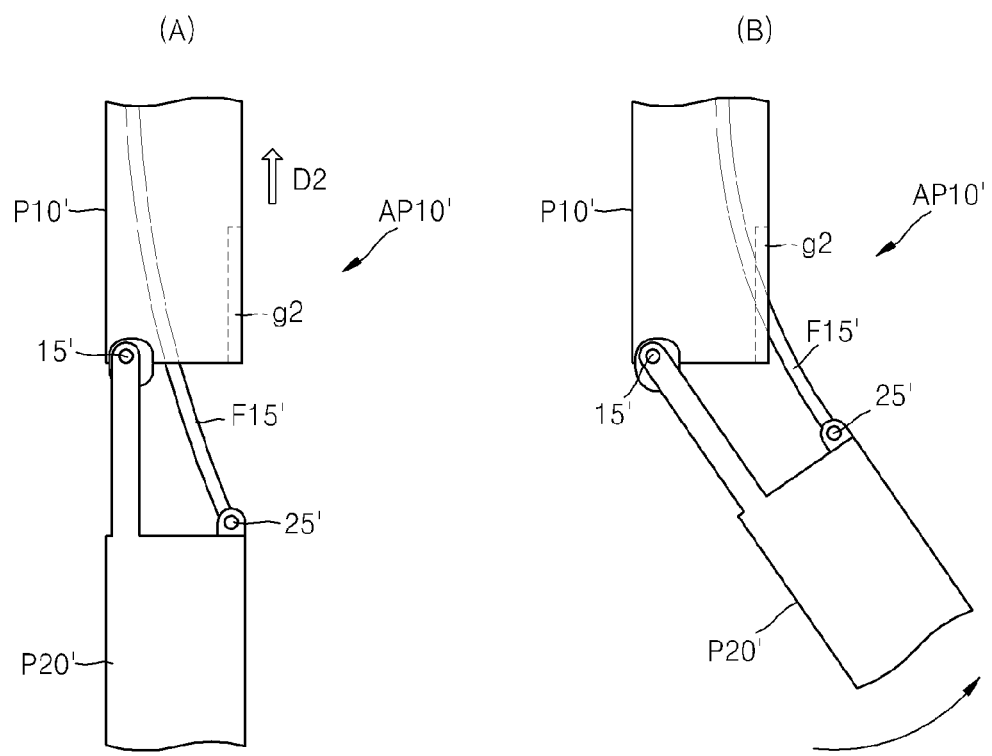
FIG. 22 is a diagram showing another example of the first joint portion of FIG. 19.

The structure of the first joint portion AP10 described with reference to FIGS. 20 and 21 may be variously modified. For example, the first joint portion AP10 of FIG. 20 may be modified into a first joint portion AP10' shown in FIG. 22. In FIG. 22, (A) denotes a state in which the first joint portion AP10' is not bent, and (B) denotes a state in which the first joint portion AP10' is bent.

Referring to (A) of FIG. 22, the first joint portion AP10' may include a first part P10', a second part P20' joined to the first part P10', and a force applying element F15' for applying a force for bending (rotating) to the second part P20'. A distance between a joint point 15' of the first part P10' with the second part P20' and a force application point 25' where a force of the force applying element F15' is applied to the second part P20' may be greater than a diameter of at least one of the first and second parts P10' and P20', for example, the second part P20'. Here, the force application point 25' may be located away from the first part P10' relative to the join position 15'. That is, the force application point 25' may be located on a portion lower than the joint point 15' in the drawings. In this case, the force application point 25' may be located on an inner portion (right portion of the drawing) of the second part P20' based on a bending (rotating) direction of the second part P20', and the joint point 15' may be located on an outer portion (left portion of the drawing) of the second part P20' based on the bending (rotating) direction of the second part P20'. That is, a relation between locations of the joint point 15' and the force application point 25' may be opposite to that of FIG. 20. For example, the joint point 15' may be disposed on a protrusion extending from the second part P20'. Meanwhile, the force applying element F15' may be formed of the same material as that of the force applying element F15 shown in FIG. 20; however, a bending direction of the force applying element F15' may be opposite to that of FIG. 20. That is, in FIG. 22, the force applying element F15' may be curved in the same direction in which the second part P20' is bent. Based on the bending direction of the second part P20', a groove g2 may be formed in an inner side of the first part P10'. The groove g2 may provide a passage through which the force applying element F15' may pass on a lower end portion of the first part P10'.

When the force applying element F15' is pulled in a second direction D2 (upper portion in FIG. 22) in (A) of FIG. 22, the second part P20' may be bent (rotated) with respect to the first part P10' as shown in (B) of FIG. 22. Since the distance between the joint point 15' and the force application point 25' is greater than the diameter of one of the first and second parts P10' and P20', for example, the second part P20', the second part P20' may be easily bent with a relatively small force. The principle of bending the second part P20' may be the same as that described with reference to FIG. 20. Therefore, the second part P20' may be easily bent with a relatively small force, and when the second part P20' is bent, a relatively strong force may be applied to the second part P20'.

Figure 23:
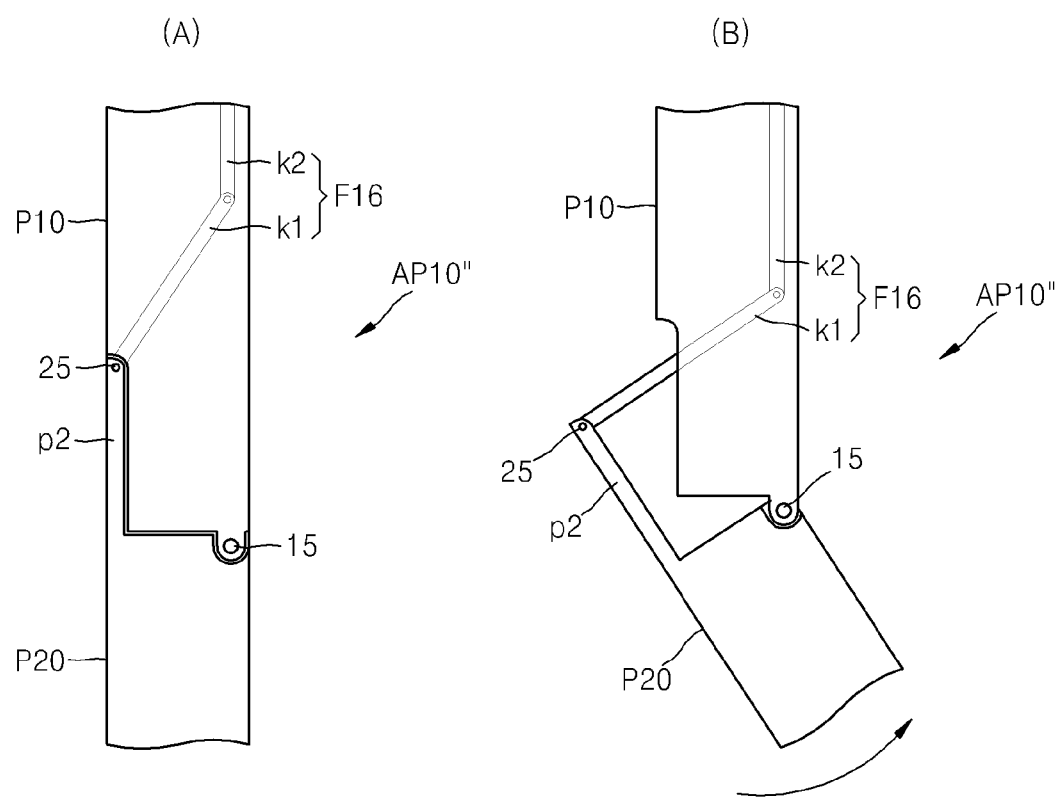
FIG. 23 is a diagram showing another example of the first joint portion of FIG. 19.

In FIGS. 20 through 22, configurations of the force applying elements F15 and F15' may be changed. In FIGS. 20 through 22, the force applying elements F15 and F15' may be single bodies formed of an elastic material; however, in another embodiment, the force applying element F15 or F15' may have a structure in which a plurality of linkage elements are connected to each other. An example of the force applying element according to another embodiment is shown in FIG. 23. FIG. 23 shows a case where a configuration of the force applying element F15 of FIG. 20 is changed.

Referring to FIG. 23, a force applying element F16 of a first joint portion AP10'' may include a plurality of linkage elements, for example, a first linkage element k1 and a second linkage element k2. Each of the first and second linkage elements k1 and k2 may have a straight appearance, and the force applying element F16 formed by linking the first and second linkage elements k1 and k2 to each other may have a curved structure. A principle of bending the second part P20 by using the force applying element F16 may be similar to that of FIG. 20. The force applying element F16 of FIG. 23 may be applied to the structure shown in FIG. 22, as well as to the structure shown in FIG. 20.

Figure 24:
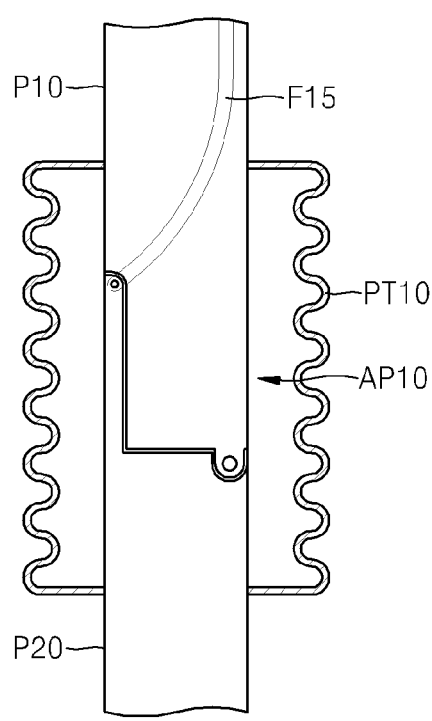
FIG. 24 is a diagram showing an example of a protective member formed on the first joint portion of FIG. 20.

The first joint portions AP10, AP10', and AP10'' described with reference to FIGS. 20 through 23 may be surrounded by predetermined protective members. For example, as shown in FIG. 24, a protective member PT10 surrounding the first joint portion AP10 may be provided. The protective member PT10 may be formed of a material that is elastic, for example, a rubber material. The protective member PT10 may have a wrinkled portion at a side surface thereof. The protective member PT10 may prevent an object from being damaged due to motion of the first joint portion AP10. In addition, the protective member PT10 may prevent impurities from infiltrating into the instrument N100 via the first joint portion AP10. A shape and a size of the protective member PT10 may be variously modified.

Hereinafter, the rotary motion portion RM10 of FIG. 19 will be described in detail with reference to FIGS. 25 and 26.

Figure 25:
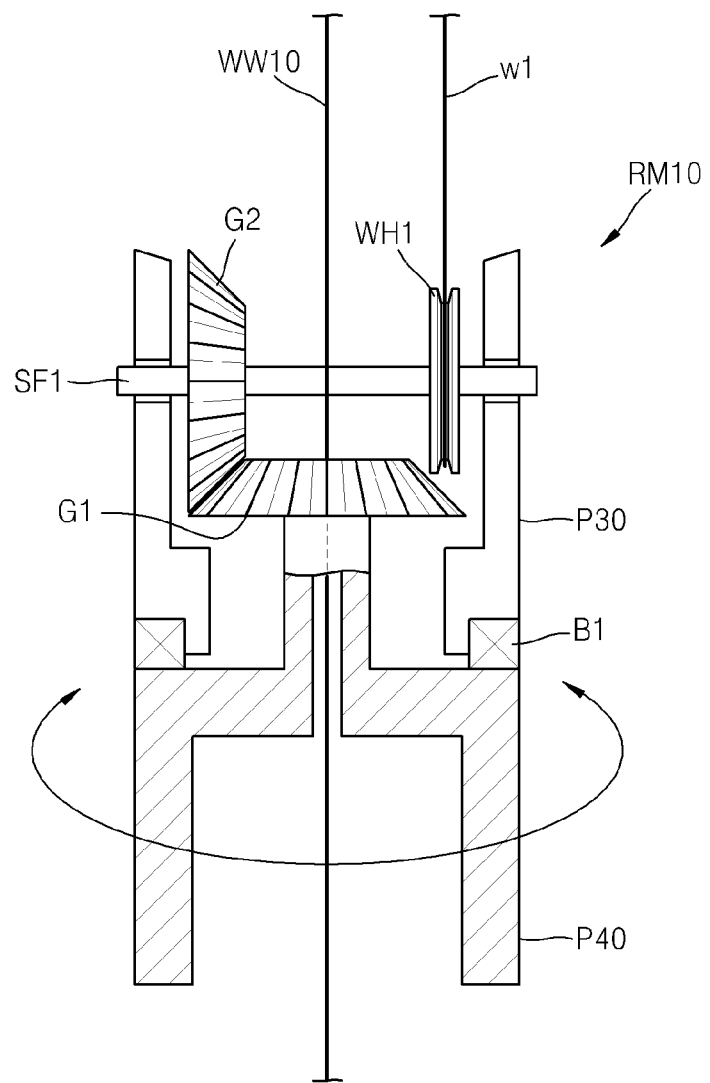
FIG. 25 is a diagram showing a configuration of a rotary motion portion of FIG. 19.

FIG. 25 is a cross-sectional view exemplary showing the rotary motion portion RM10 of FIG. 19.

Referring to FIG. 25, the rotary motion portion RM10 may include a third part P30 and a fourth part P40. The third part P30 may be extended from the second part P20 of FIG. 20. Therefore, the third part P30 may be integrally formed with the second part P20 of FIG. 20. A bearing B1 may be disposed between the third part P30 and the fourth part P40. A first gear G1 may be connected to an end portion of the fourth part P40 to be inserted into the third part P30. A second gear G2 may be engaged with the first gear G1. The second gear G2 may be disposed to be perpendicular to the first gear G1 at an end portion of the first gear G1. A shaft SF1 may penetrate through a center portion of the second gear G2. The shaft SF1 may be a rotating axis. Opposite end portions of the shaft SF1 may be inserted in the third part P30. A wheel WH1 in which the shaft SF1 is inserted may be further provided, and a wire (or cable) w1 may be attached to the wheel WH1. When the wheel WH1 is rotated by using the wire w1, the second gear G2 may be rotated due to rotation of the shaft SF1, and the first gear G1 engaged with the second gear G2 may be rotated. Therefore, the fourth part P40 may roll. A rotating direction of the second gear G2 may vary depending on a rotating direction of the wheel WH1, and consequently, the rotating direction of the fourth part P40 may vary. For example, the fourth part 40 may rotate in a clockwise or counterclockwise direction about a longitudinal axis of the rotary motion portion RM10 or about the axis corresponding to wires WW10 which pass through an inner portion of the rotary motion portion RM10

As mentioned above, FIG. 25, reference numeral WW10 denotes a plurality of wires. The plurality of wires WW10 may pass through an inner portion of the rotary motion portion RM10. The plurality of wires WW10 may be connected to the second joint portion AP20 and the surgical tool ST10 shown in FIG. 19, and may be used to drive motions of the second joint portion AP20 and the surgical tool ST10. The plurality of wires WW10 may be connected to a plurality of surgical tools if a plurality of surgical tools are attached to the second joint portion AP20.

The structure of the rotary motion portion RM10 shown in FIG. 25 is an example, and the rotary motion portion RM10 may be modified variously. A modified example of the rotary motion portion RM10 is shown in FIG. 26. FIG. 26 shows another example of a rotary motion portion RM10'.

Figure 26:
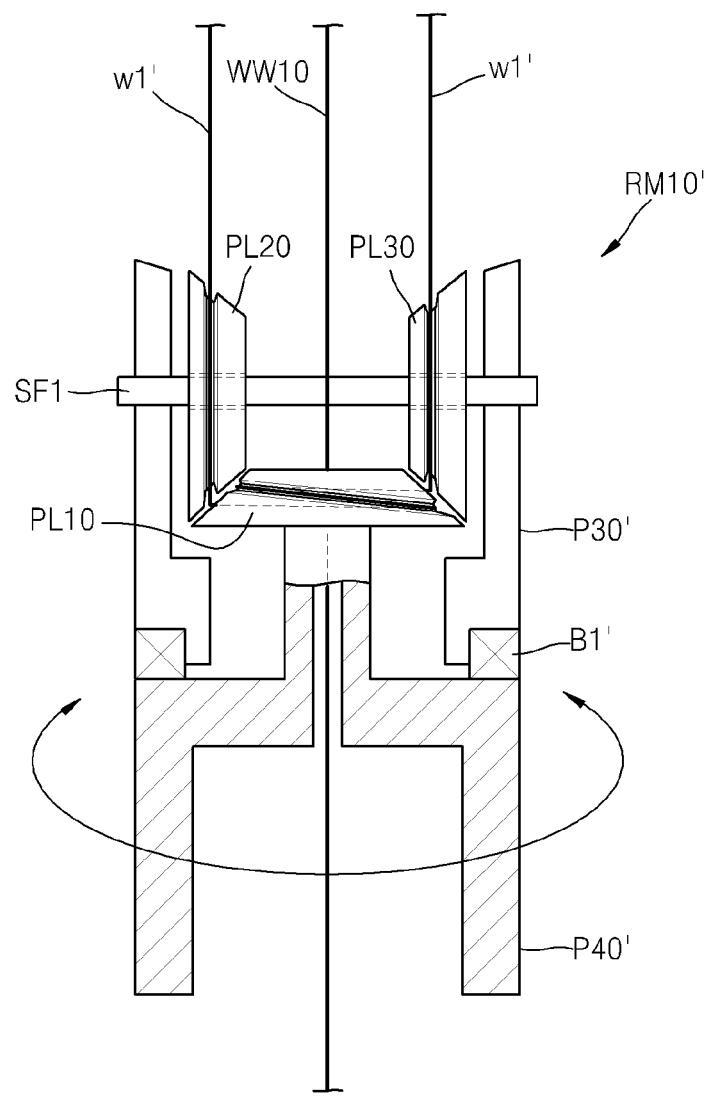
FIG. 26 is a diagram showing another example of the rotary motion portion of FIG. 19.

Referring to FIG. 26, the rotary motion portion RM10' may include a third part P30' and a fourth part P40', and a bearing B1' may be disposed between the third part P30' and the fourth part P40'. A first pulley PL10 may be connected to an end portion of the fourth part P40' and may be inserted into the third part P30'. A side surface of the first pulley PL10 may be inclined at about an angle of 45° or a similar angle. A second pulley PL20 and a third pulley PL30 may be adjacent to opposite ends of the first pulley PL10. The second and third pulleys PL20 and PL30 may be perpendicular to the first pulley PL10. Like the first pulley PL10, side surfaces of the second and third pulleys PL20 and PL30 may be inclined. A shaft SF1' on which the second and third pulleys PL20 and PL30 are disposed may be provided. Opposite ends of the shaft SF1' may be inserted in the third part P30' to be fixed. The second and third pulleys PL20 and PL30 may be disposed on the shaft SF1' to be rotated independently from each other. A wire w1' may be attached to the first, second, and third pulleys PL10, PL20, and PL30. The wire w1' may be wound on a side surface portion of the first pulley PL10, and an end of the wire w1' may be wound on the second pulley PL20 to be extended toward a head portion (upper portion in FIG. 26) and the other end of the wire w1' may be wound on the third pulley PL30 to be extended toward the head portion (upper portion in FIG. 26). A recess may be formed in the side surface of each of the first through third pulleys PL10 through PL30 so that the wire w1' may be attached thereon easily. When the wire w1' is pulled toward one of the second and third pulleys PL20 and PL30, the wire w1' moves and the first pulley PL10 may be rotated, thereby rolling the fourth part P40'. A rotating direction of the first pulley PL10 may be determined according to which one of the second and third pulleys PL20 and PL30 pulls the wire w1', and accordingly a rolling direction of the fourth part P40' is determined.

The rotary motion portion RM10 described with reference to FIG. 25 is a gear type, and the rotary motion portion RM10' described with reference to FIG. 26 is a pulley type. However, the rotary motion portions described with reference to FIGS. 25 and 26 are examples, and may be variously modified.

Hereinafter, the head portion H10 shown in FIG. 19 will be described in more detail with reference to FIGS. 27 through 29.

Figure 27:
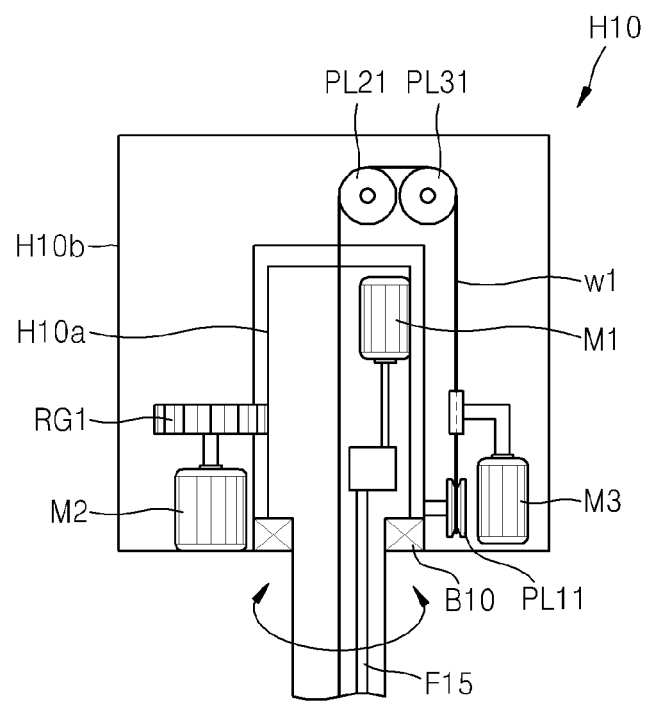
FIG. 27 is a diagram showing a configuration of a head portion of FIG. 19.

FIG. 27 exemplarily shows a configuration of the head portion H10 shown in FIG. 19.

Referring to FIG. 27, the head portion H10 may include an inner head portion H10a and an outer head portion H10b surrounding the inner head portion H10a. A bearing B10 may be disposed between the inner head portion H10a and the outer head portion H10b. The bearing B10 may be located on a lower circumference of the inner head portion H10a. The outer head portion H10b may contact the bearing B10 while surrounding the inner head portion H10a. Due to the above structure, the inner head portion H10a may be rotated in a state where the outer head portion H10b is fixed.

The inner head portion H10a may include a first motor M1 that is connected to the force applying element F15. The first motor M1 may be, for example, a linear motor. The force applying element F15 connected to the first motor M1 may be the force applying element F15 described with reference to FIG. 20. The force applying element F15 may be reciprocated in an up and down direction by driving the first motor M1. Due to movement of the force applying element F15 in the up and down direction, the first joint portion AP10 may perform a pitch motion as described with reference to FIG. 20.

The outer head portion H10b may include a second motor M2. The second motor M2 may be a rotary motor. A roll gear RG1 may be connected to the second motor M2. The roll gear RG1 may be engaged with the inner head portion H10a. The roll gear RG1 rotates when driven by the second motor M2, and accordingly the inner head portion H10a may be rotated. Since the inner head portion H10a is connected to the instrument N100, except for the head portion H10, the entire instrument N100 may roll due to rotation of the inner head portion H10a. Here, the outer head portion H10b may be fixed by a predetermined support element (not shown). That is, in a state where the outer head portion H10b is fixed by the support element, the remaining instrument N100 may perform a rolling movement due to rotation of the inner head portion H10a.

The outer head portion H10b may further include one or more motors. In FIG. 27, only a third motor M3 is shown; however, one or more additional motors may be further disposed. The third motor M3 may be a linear motor. The third motor M3 may be connected to a wire w1 to control movement of the wire w1. The wire w1 may be inserted in the instrument N100. The wire w1 may be, for example, the wire w1 of the rotary motion portion RM10 described with reference to FIG. 25. The wire w1 may be wound on a first pulley PL11 that is fixed on a lower portion of the outer head portion H10b, and then inserted in the inner head portion H10a via a plurality of pulleys PL21 and PL31 disposed on an upper portion of the outer head portion H10b to be inserted in the instrument N100 under the inner head portion H10a. In FIG. 27, there are three pulleys shown disposed in the head portion H10. However, there may be more than or less than three pulleys disposed in the head portion H10.

Figure 28:
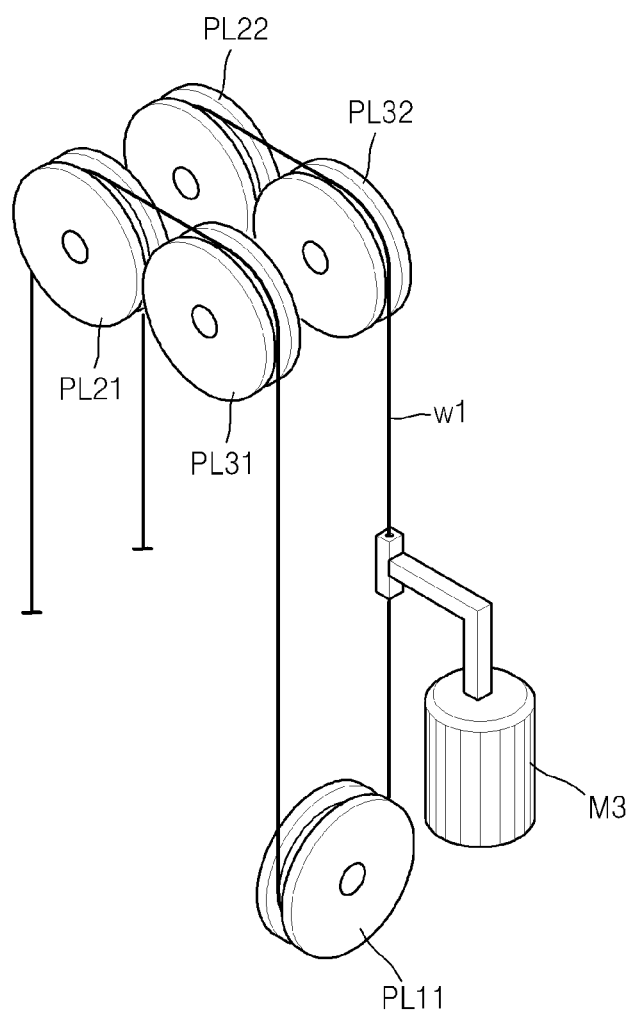
FIG. 28 is a perspective view showing some elements shown in FIG. 27.

FIG. 28 shows the third motor M3, the wire w1, and the pulleys PL11, PL21, and PL31. As shown in FIG. 28, the third motor M3 may be connected to a portion of the wire w1 to make the wire w1 move in an up-and-down direction. A plurality of pulleys PL22 and PL32 forming pairs with the plurality of pulleys PL21 and PL31 formed on the upper portion may be further provided. The wire w1 is an element having a band (loop) shape; however, the wire w1 may be considered as two wires since the wire w1 is divided into two parts between opposite end portions. Here, the wire w1 may be considered as two wires.

Figure 29:
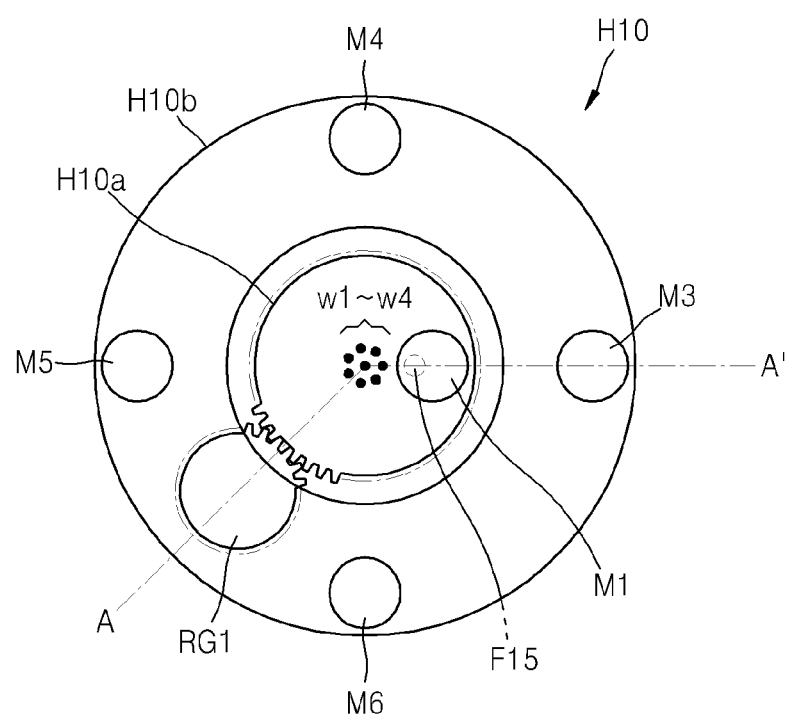
FIG. 29 is a plan view of principal elements of the head portion of FIG. 27 when the head portion is seen from above.

FIG. 29 is a plan view showing principal elements of the head portion H10 of FIG. 27 when the head portion H10 is seen from above. FIG. 27 may be a cross-sectional view of the head portion H10 taken along a line A-A' of FIG. 29.

Referring to FIG. 29, the inner head portion H10a is provided, and the outer head portion H10b may surround the inner head portion H10a. The first motor M1 may be disposed in the inner head portion H10a, and the first motor M1 may be connected to the force applying element F15. The roll gear RG1 may be disposed in the outer head portion H10b, and the roll gear RG1 may be engaged with the inner head portion H10a. The second motor (not shown, M2 of FIG. 27) for driving the roll gear RG1 may be disposed in the outer head portion H10b, for example. Further, the roll gear RG1 may be engaged with the inner head portion H10a and may be meshed together via teeth disposed on an outer surface portion of the inner head portion H10a. At least one or more motors may be further disposed in the outer head portion H10b. For example, four motors (hereinafter, third through sixth motors M3 through M6) may be further arranged. Each of the third through sixth motors M3 through M6 may control movement of each of first through fourth wires w1 through w4. The first wire w1 may be connected to the rotary motion portion RM10, the second and third wires w2 and 23 may be connected to the second joint portion AP20, and the fourth wire w4 may be connected to the surgical tool ST10. Each of the first through fourth wires w1 through w4 may be considered as two wires, as described in FIG. 28. Therefore, the four wires w1 through w4 may be considered as eight wires in total. The total number of wires may vary depending on the structures of the joint portions AP10 and AP20 and the surgical tool ST10 of the instrument N100. As the total degree of freedom of the instrument increases, the number of wires may increase. In addition, the number of motors may vary, and may be more or less than six motors. The number of motors may be determined based on a variety of factors including the number of surgical tools, the number of degrees of freedom desired in the joint portions, rotary motion portions and surgical tools, the number of wires, among other things.

The structure of the head portion H10 described with reference to FIGS. 27 through 29 is an example, and may be variously modified.

The instrument N100 described with reference to FIGS. 19 through 29 may operate with a relatively large force by using the first joint portion AP10, AP10', or AP10", and may have a relatively large workspace. That is, the instrument N100 may ensure a relatively high operating force and a relatively large workspace due to the first joint portion AP10, AP10', or AP10". In addition, the instrument N100 may perform a dexterous motion with a high degree of freedom by using the first joint portion AP10, AP10', or AP10", the second joint portion AP20, and the rotary motion portion RM10 or RM10' disposed between the first and second joint portions. Moreover, the entire instrument N100 (except for the head portion H10) may perform a rolling movement due to the head portion H10, and the surgical tool ST10 may operate with at least one degree of freedom. Therefore, the instrument N100 may move with at least six degrees of freedom. Accordingly, a surgical operation may be performed effectively and skillfully by using the instrument N100.

The instrument N100 described with reference to FIGS. 19 through 29 may be mounted in the supporter device 100 or 100a described with reference to FIGS. 3 through 18, and the above configuration may be applied to the surgical robot system shown in FIG. 1 (that is, the surgical manipulation system). Here, the supporter device 100 or 100a may provide an RCM movement of the instrument N100. Since the instrument N100 may be driven with multiple degrees of freedom due to the supporter device 100 or 100a on the outer portion of the incision port (30 of FIG. 1), a relatively large force may be transferred to the instrument N100. That is, since the instrument N100 is moved by using a relatively large actuator, that is, the supporter device 100 or 100a, on the outer portion of the incision port, it is easy to transfer a relatively large force to the instrument N100. Therefore, an operating force of the instrument N100 may be increased.

Also, some motions of the instrument N100 are controlled by the supporter device 100 or 100a on the outer portion of the incision port, and thus it is not necessary to arrange a lot of driving elements (for example, a connecting element such as a wire) in the instrument N100. Therefore, sizes of the driving elements (for example, the connecting element such as the wire) in the instrument N100 may be increased, and accordingly, an operating force of the driving element may be improved, which increases an operating force of the instrument N100.

Moreover, the instrument N100 is moved by using the supporter device 100 or 100a on the outer portion of the incision port, and the instrument N100 itself may move the joint portions AP10 and AP20 and the rotary motion portion RM10, and accordingly a relatively large workspace may be ensured. In particular, when a plurality of instruments N100 are mounted in the supporter device 100a described with reference to FIGS. 14 through 18 to perform a surgical operation, simultaneous and cooperative operations may be easily performed through a single incision port without interferences between the plurality of instruments N100, and a relatively larger workspace may be ensured.

Therefore, according to the supporter device 100 or 100a, the instrument N100, and the surgical robot system (that is, the surgical manipulation system) including the supporter device and the instrument of the present invention, a surgical operation may be performed effectively through an incision port of a relatively small size.

In the above embodiments, some of the components constituting the surgical robot system including the surgery station and one or more control stations may be realized by a kind of module. The module may include software components or hardware components, such as a field programmable gate array (FPGA) or an application specific integrated circuit (ASIC), to perform a specific function. However, the module is not limited to software or hardware. The module may be configured to be present in an addressable storage medium or to execute one or more processors. The one or more processors may include a microprocessor, central processing unit (CPU), digital signal processor (DSP), or application-specific integrated circuit (ASIC), as well as portions or combinations of these and other processing devices.

By way of example, the module may include components, such as software components, object-oriented software components, class components, and task components, processes, functions, attributes, procedures, subroutines, segments of a program code, drivers, firmware, microcode, circuitry, data, databases, data structures, tables, arrays, and variables. Functions provided by the components and modules may be combined into fewer components and modules or further divided into additional components and modules. In addition, the components and modules may execute one or more central processing units (CPUs) in a device.

In addition to the above embodiments, embodiments of the present invention may also be realized by a medium including a computer readable code/command to control at least one processing element of the above embodiments, e.g. a computer readable medium. The medium may correspond to any medium/media enabling the storage and/or transmission of the computer readable code.

The computer readable code may be recorded in a medium or transmitted through the Internet. The medium may include a recording medium, such as a magnetic storage medium (for example, a ROM, a floppy disk, or a hard disk) or an optical medium (for example, a compact disk read only memory (CD-ROM) or a digital versatile disk (DVD)), or a transmission medium, such as a carrier wave. Also, according to embodiments of the present invention, the medium may be a signal, such as a composite signal or a bitstream. The medium may also be a distributed network, and therefore, the computer readable code may be stored/transmitted and executed in a distributed fashion. In addition, for example, a processing element may include a processor or a computer processor. The processing element may be distributed and/or included in a device.

The disclosure herein has provided example embodiments of a surgical robot system and control methods thereof, which may be applied for example, in a medical setting to perform an operation on a patient (e.g., a human or animal or other lifeform). However, the disclosure is not so limited. For example, the surgical robot system may be used in other settings which may benefit from the example embodiments disclosed herein. For example, the surgical robot system may be utilized to perform operations in any confined space or enclosure in which an operator may need to perform controlled movements using an instrument attached to a supporter device, so as to avoid or to prevent injuries to bodies or objects, that may be located or disposed within the space or enclosure, due to imprecise movements of the surgical robot. Possible settings may include, for example, mining operations, surveillance operations, inspection operations, repair operations, bomb disposal operations, etc., however again, the disclosure is not so limited.

It should be understood that the exemplary embodiments described therein should be considered in a descriptive sense only and not for purposes of limitation. Descriptions of features or aspects within each embodiment should typically be considered as available for other similar features or aspects in other embodiments. For example, one of ordinary skill in the art where the present invention belongs to would have appreciated that the supporter device, the instrument, and the surgical robot system (the surgical manipulation system) according to the above embodiments of the present invention may be variously modified. Also, one of ordinary skill in the art would have appreciated that the supporter device and the instrument according to the embodiments of the present invention may be applied to other equipment, as well as surgical equipment (system). Therefore, the scope of the invention is defined not by the detailed description of the invention but by the appended claims, and all differences within the scope will be construed as being included in the present invention.

What is claimed is:

1. A surgical manipulation system comprising:
   a supporting structure;
   at least one instrument supported by the supporting structure; and
   an operating device configured to operate the instrument,
   wherein the instrument comprises a first joint portion configured to perform a motion with at least one degree of freedom,
   the first joint portion includes a first part, a second part connected to the first part to be bent with respect to the first part, and a force applying element connected to the second part to apply a force for bending the second part,
   a distance between a joint point which joins the first part with the second part and a force application point where a force is applied to the second part from the force applying element is greater than a diameter of at least one of the first part and the second part, the force application point being a portion of the second part, and no connecting link provided between the force application point and the force applying element, and
   at least one of the first part or the second part includes a cylindrical portion, the cylindrical portion having a circular horizontal cross-section, and the diameter is a length of a straight line drawn across the circular horizontal cross-section while passing through a center thereof,
   the force application point is disposed above the joint point in a vertical direction, the force application point is located on an outer side of the second part based on a direction in which the second part is bent, and the joint point is located on an inner side of the second part based on the direction in which the second part is bent,
   a protrusion protruding toward the first part is formed on an end portion of the second part, and the force applying element is connected to an end portion of the protrusion, and
   the first part comprises a groove to receive the protrusion of the second part.

2. The surgical manipulation system of claim 1, wherein the distance between the joint point and the force application point is about 1.5 to about 3 times longer than the diameter of the first part or the second part.

3. The surgical manipulation system of claim 1, wherein the force applying element is an elastic body.

4. The surgical manipulation system of claim 3, wherein the force applying element has a curved structure.

5. The surgical manipulation system of claim 1, wherein the force applying element has a structure in which a plurality of linkage elements are connected to each other.

6. The surgical manipulation system of claim 1, wherein the instrument further comprises a rotary motion portion adjacent to the first joint portion.

7. The surgical manipulation system of claim 1, wherein the instrument further comprises:
   a second joint portion spaced apart from the first joint portion; and
   a surgical tool connected to an end portion of the second joint portion.

8. The surgical manipulation system of claim 7, wherein the second joint portion is configured to move with at least two degrees of freedom.

9. The surgical manipulation system of claim 7, wherein the instrument further comprises a rotary motion portion disposed between the first joint portion and the second joint portion, and a lower portion of the instrument including the second joint portion is configured to perform a rolling motion via the rotary motion portion.

10. The surgical manipulation system of claim 1, further comprising:

a driving unit configured to control one or more motions of the instrument, the driving unit being disposed on a head of the instrument.

11. The surgical manipulation system of claim 1, wherein the supporting structure comprises a remote center of motion (RCM) structure to provide a RCM point of the at least one instrument.

12. The surgical manipulation system of claim 11, wherein the RCM structure comprises a cone-type structure having a hole in a center portion thereof, and the at least one instrument is inserted in the hole.

13. The surgical manipulation system of claim 11, wherein the at least one instrument comprises a first instrument and a second instrument, and an RCM point of the first instrument and an RCM point of the second instrument are separated from each other.

14. The surgical manipulation system of claim 11, wherein the RCM structure is configured to drive the at least one instrument with three degrees of freedom.

15. The surgical manipulation system of claim 1, further comprising:
    an imaging device for photographing a region where the at least one instrument operates; and
    a display device for displaying images obtained by the imaging device.

16. The surgical manipulation system of claim 1, wherein the force applying element includes an elastic material.

17. The surgical manipulation system of claim 1, wherein the supporting structure includes,
    a base including an insertion region, the insertion region configured to pass an extension portion of the instrument therethrough,
    a movable member movably coupled to the base and configured to move around the insertion region along a circular moving path based on a movable central axis, the movable central axis penetrating through the insertion region, and
    a pivot member coupled on and rotatably supported by the movable member, the pivot member configured to rotate based on a pivot axis, the pivot member including a mounting portion, the mounting portion configured to mount the instrument thereon.

18. The surgical manipulation system of claim 17, wherein the supporting structure is configured to move the instrument with at least two degrees of freedom with respect to a single point by configuring the movable central axis, the pivot axis, and an extension axis of the instrument mounted on the pivot member to cross at the single point.

19. A surgical instrument comprising at least one joint portion, the joint portion comprises:
    a first part;
    a second part connected to the first part to be bent with respect to the first part; and
    a force applying element connected to the second part to apply a force to bend the second part, and
    wherein a distance between a joint point which joins the first part with the second part and a force application point where a force is applied to the second part from the force applying element is greater than a diameter of at least one of the first part and the second part, the force application point is a portion of the second part, and no connecting link is provided between the force application point and the force applying element,
    at least one of the first part or the second part includes a cylindrical portion, the cylindrical portion having a circular horizontal cross-section, and the diameter is a length of a straight line drawn across the circular horizontal cross-section while passing through a center thereof,
    the force application point is disposed above the joint point in a vertical direction, the force application point is located on an outer side of the second part based on a direction in which the second part is bent, and the joint point is located on an inner side of the second part based on the direction in which the second part is bent,
    a protrusion protruding toward the first part is formed on an end portion of the second part, and the force applying element is connected to an end portion of the protrusion, and
    the first part comprises a groove to receive the protrusion of the second part.

20. The surgical instrument of claim 19, wherein the force application point is disposed nearer a first end of the first part relative to the joint point.

21. The surgical instrument of claim 19, wherein the distance between the joint point and the force application point is about 1.5 to about 3 times longer than the diameter of the first part or the second part.

22. The surgical instrument of claim 19, wherein the force applying element is an elastic body.

23. The surgical instrument of claim 22, wherein the force applying element has a curved structure.

24. The surgical instrument of claim 19, wherein the force applying element has a structure in which a plurality of linkage elements are connected to each other.

25. The surgical instrument of claim 19, wherein the surgical instrument further comprises a rotary motion portion adjacent to the joint portion.

26. The surgical instrument of claim 19, further comprising:
    a second joint portion spaced apart from the joint portion; and
    a surgical tool connected to an end portion of the second joint portion.

27. The surgical instrument of claim 26, wherein a rotary motion portion is further disposed between the joint portion and the second joint portion, and a lower portion of the surgical instrument including the second joint portion is configured to roll due to the rotary motion portion.

* * * * *